(12) United States Patent
Gambhir et al.

(10) Patent No.: US 8,076,159 B2
(45) Date of Patent: Dec. 13, 2011

(54) LIGAND-REGULABLE TRANSACTIVATION SYSTEMS, METHODS OF USE THEREOF, METHODS OF DETECTING ESTROGEN RECEPTOR LIGANDS, AND METHODS OF DIFFERENTIATING ESTROGEN RECEPTOR LIGAND AGONISTS AND ANTAGONISTS

(75) Inventors: Sanjiv S. Gambhir, Portola Valley, CA (US); Ramasamy Paulmurugan, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 12/658,528

(22) Filed: Feb. 10, 2010

(65) Prior Publication Data

US 2010/0169993 A1 Jul. 1, 2010

Related U.S. Application Data

(62) Division of application No. 11/890,114, filed on Aug. 3, 2007, now Pat. No. 7,709,253.

(60) Provisional application No. 60/835,674, filed on Aug. 4, 2006.

(51) Int. Cl.
*G01N 33/566* (2006.01)
*G01N 33/53* (2006.01)
*G01N 33/567* (2006.01)
*C12Q 1/70* (2006.01)
*C12Q 1/66* (2006.01)
*C12N 5/00* (2006.01)
*C12N 5/07* (2010.01)
*C12N 5/10* (2006.01)

(52) U.S. Cl. ........ 436/501; 436/814; 435/7.8; 435/6.13; 435/7.1; 435/7.21; 435/8; 435/325; 435/354; 435/361

(58) Field of Classification Search .......... None
See application file for complete search history.

(56) References Cited

U.S. PATENT DOCUMENTS

| 5,939,442 | A | * | 8/1999 | Evans et al. | 514/357 |
|---|---|---|---|---|---|
| 6,828,103 | B2 | | 12/2004 | Herrington et al. | 435/6 |
| 6,884,577 | B2 | | 4/2005 | Kushner et al. | 435/6 |
| 7,094,559 | B1 | | 8/2006 | Harnish et al. | 435/8 |
| 7,135,550 | B2 | | 11/2006 | Come et al. | 530/350 |
| 7,157,604 | B2 | | 1/2007 | Meng et al. | 564/308 |
| RE39,708 | E | | 6/2007 | Huebner et al. | |
| 7,381,813 | B2 | * | 6/2008 | Bracken et al. | 536/23.5 |
| 7,628,229 | B2 | | 12/2009 | Wood et al. | 544/242 |
| 2003/0143559 | A1 | | 7/2003 | Bracken et al. | 435/6 |
| 2003/0166281 | A1 | | 9/2003 | Foulkes et al. | |
| 2005/0153310 | A1 | | 7/2005 | Fan et al. | |
| 2005/0204416 | A1 | * | 9/2005 | Hamilton et al. | 800/278 |
| 2005/0260643 | A1 | | 11/2005 | Hung et al. | 435/6 |
| 2006/0223141 | A1 | | 10/2006 | Carey et al. | 435/69.1 |

FOREIGN PATENT DOCUMENTS

WO WO 03/000856 1/2003

OTHER PUBLICATIONS

Hunt et al. 2002. Science 297:415-416.*
Romano et al 2003. Drug News Perspect. 16:267-276.*
Dahlman-Wright et al. 2006. Pharm Rev. 58: 773-781.

* cited by examiner

*Primary Examiner* — Shulamith H Shafer
(74) *Attorney, Agent, or Firm* — Thomas, Kayden, Horstemeyer & Risley, LLP

(57) ABSTRACT

Briefly described, embodiments of this disclosure include ligand-regulable transactivation systems, methods of producing ligand-regulable transactivation systems, methods of using ligand-regulable transactivation systems, reporter polynucleotides, method of producing reporter polynucleotides, activator fusion proteins, methods of producing activator fusion proteins, methods of regulating gene expression in vitro and in vivo for gene therapy, methods of screening estrogen receptor modulators with therapeutic treatments (e.g., anticancer, antiosteoporosis, and hormone replacement treatments), method of screening compounds (e.g., drugs and environmental pollutants) for the estrogenic effect, methods of evaluating the estrogen receptor pathway under different pathological conditions are provided, and the like.

19 Claims, 10 Drawing Sheets

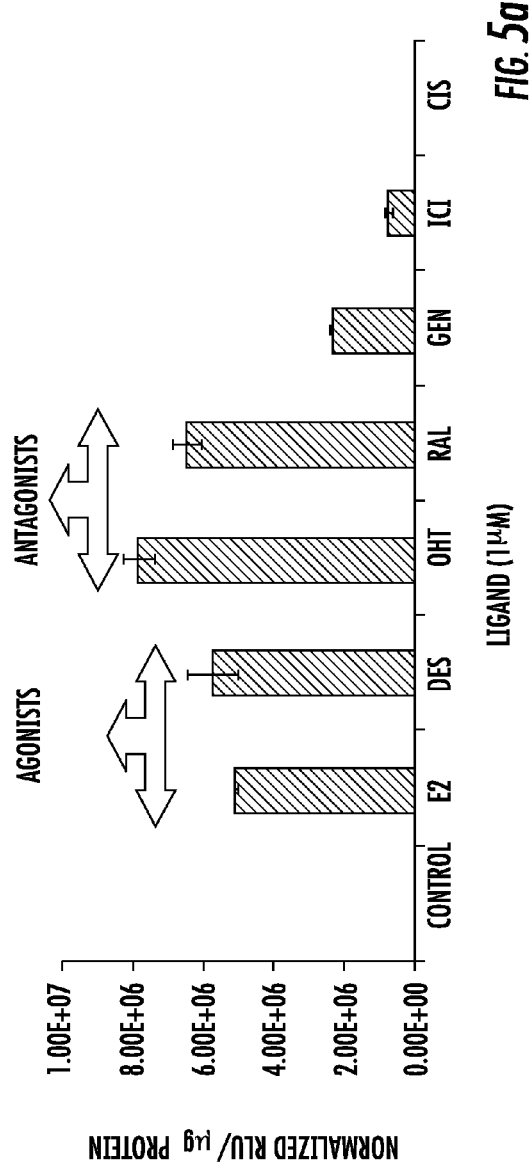
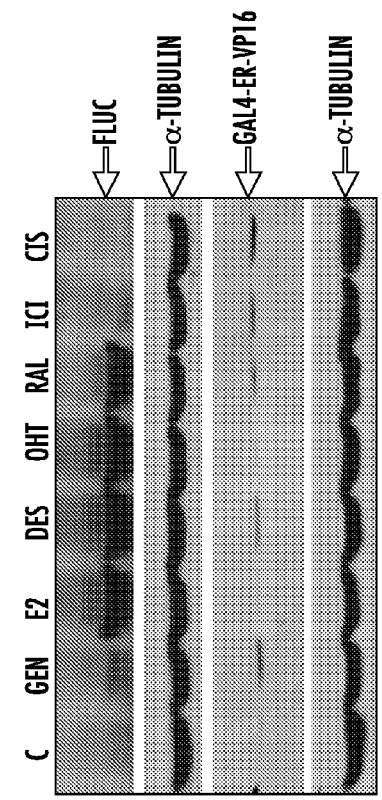
FIG. 5a
FIG. 5b

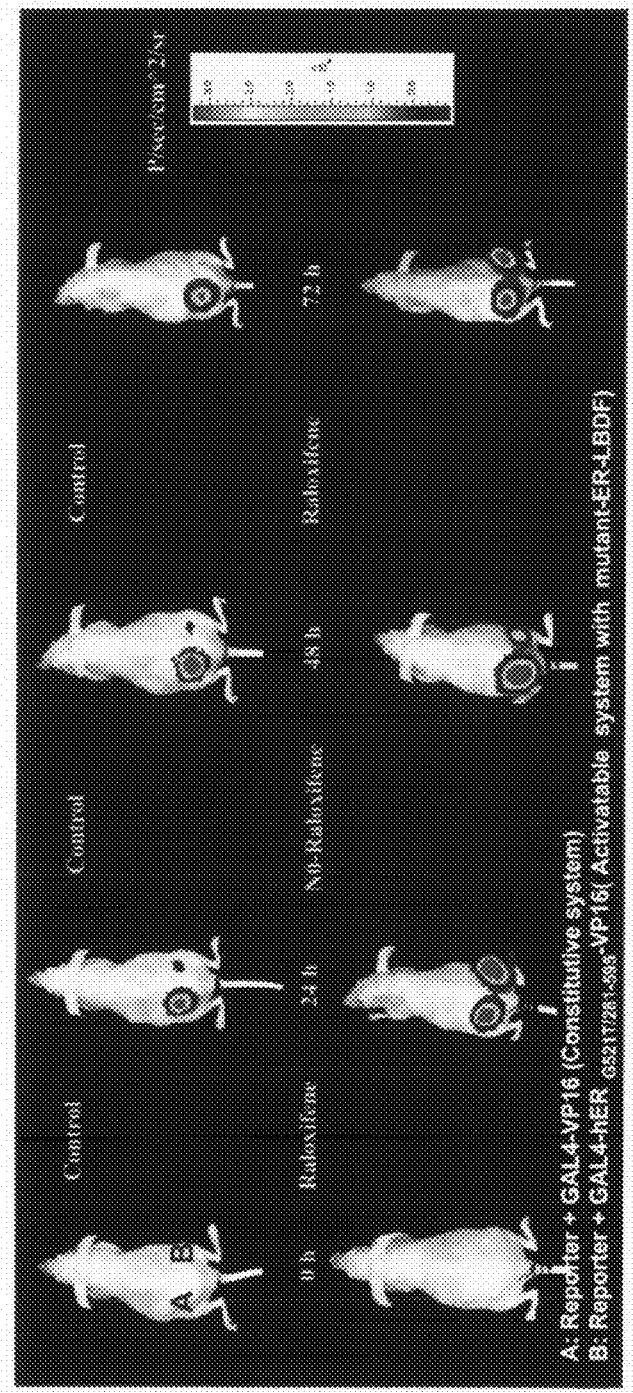
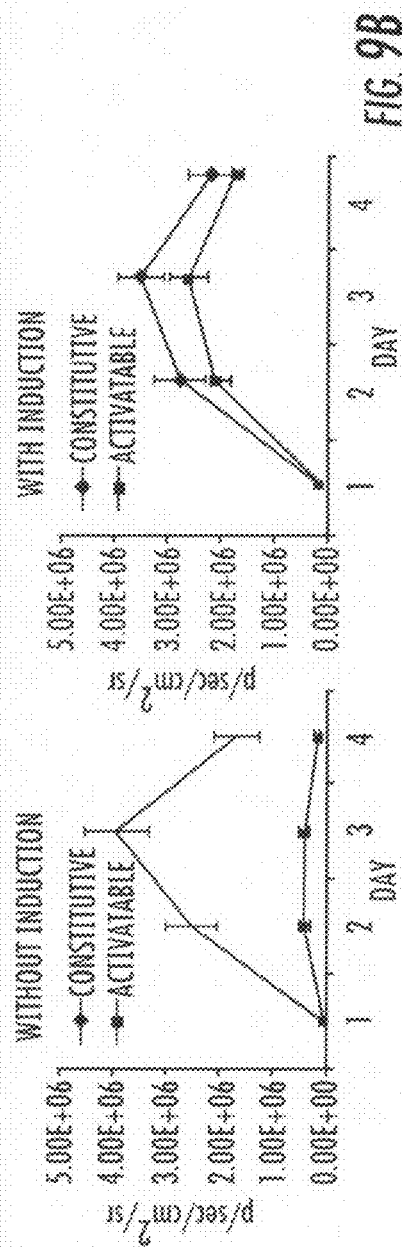
FIG. 9A
FIG. 9B

SEQUENCE LISTING

<160> NUMBER OF SEQ ID NOS: 38

<210> SEQ ID NO 1
<211> LENGTH: 269
<212> TYPE: PRT
<213> ORGANISM: Homo Sapien

<400> SEQUENCE: 1

```
Gly Ser Ala Gly Asp Met Arg Ala Ala Asn Leu Trp Pro Ser Pro Leu
1               5                   10                  15

Met Ile Lys Arg Ser Lys Lys Asn Ser Leu Ala Leu Ser Leu Thr Ala
            20                  25                  30

Asp Gln Met Val Ser Ala Leu Leu Asp Ala Glu Pro Pro Ile Leu Tyr
        35                  40                  45

Ser Glu Tyr Asp Pro Thr Arg Pro Phe Ser Glu Ala Ser Met Met Gly
    50                  55                  60

Leu Leu Thr Asn Leu Ala Asp Arg Glu Leu Val His Met Ile Asn Trp
65                  70                  75                  80

Ala Lys Arg Val Pro Gly Phe Val Asp Leu Thr Leu His Asp Gln Val
                85                  90                  95

His Leu Leu Glu Cys Ala Trp Leu Glu Ile Leu Met Ile Gly Leu Val
            100                 105                 110

Trp Arg Ser Met Glu His Pro Val Lys Leu Leu Phe Ala Pro Asn Leu
        115                 120                 125

Leu Leu Asp Arg Asn Gln Gly Lys Cys Val Glu Gly Met Val Glu Ile
    130                 135                 140

Phe Asp Met Leu Leu Ala Thr Ser Ser Arg Phe Arg Met Met Asn Leu
145                 150                 155                 160

Gln Gly Glu Glu Phe Val Cys Leu Lys Ser Ile Ile Leu Leu Asn Ser
                165                 170                 175

Gly Val Tyr Thr Phe Leu Ser Ser Thr Leu Lys Ser Leu Glu Glu Lys
```

```
            180                 185                 190
Asp His Ile His Arg Val Leu Asp Lys Ile Thr Asp Thr Leu Ile His
            195                 200                 205

Leu Met Ala Lys Ala Gly Leu Thr Leu Gln Gln Gln His Gln Arg Leu
210                 215                 220

Ala Gln Leu Leu Leu Ile Leu Ser His Ile Arg His Met Ser Asn Lys
225                 230                 235                 240

Gly Met Glu His Leu Tyr Ser Met Lys Cys Lys Asn Val Val Pro Leu
                245                 250                 255

Tyr Asp Leu Leu Leu Glu Met Leu Asp Ala His Arg Leu
            260                 265
```

<210> SEQ ID NO 2
<211> LENGTH: 315
<212> TYPE: PRT
<213> ORGANISM: Homo Sapien

<400> SEQUENCE: 2

```
Gly Ser Ala Gly Asp Met Arg Ala Ala Asn Leu Trp Pro Ser Pro Leu
1               5                   10                  15

Met Ile Lys Arg Ser Lys Lys Asn Ser Leu Ala Leu Ser Leu Thr Ala
                20                  25                  30

Asp Gln Met Val Ser Ala Leu Leu Asp Ala Glu Pro Pro Ile Leu Tyr
            35                  40                  45

Ser Glu Tyr Asp Pro Thr Arg Pro Phe Ser Glu Ala Ser Met Met Gly
        50                  55                  60

Leu Leu Thr Asn Leu Ala Asp Arg Glu Leu Val His Met Ile Asn Trp
65              70                  75                  80

Ala Lys Arg Val Pro Gly Phe Val Asp Leu Thr Leu His Asp Gln Val
                85                  90                  95

His Leu Leu Glu Cys Ala Trp Leu Glu Ile Leu Met Ile Gly Leu Val
            100                 105                 110

Trp Arg Ser Met Glu His Pro Val Lys Leu Leu Phe Ala Pro Asn Leu
        115                 120                 125

Leu Leu Asp Arg Asn Gln Gly Lys Cys Val Glu Gly Met Val Glu Ile
    130                 135                 140

Phe Asp Met Leu Leu Ala Thr Ser Ser Arg Phe Arg Met Met Asn Leu
145                 150                 155                 160

Gln Gly Glu Glu Phe Val Cys Leu Lys Ser Ile Ile Leu Leu Asn Ser
                165                 170                 175

Gly Val Tyr Thr Phe Leu Ser Ser Thr Leu Lys Ser Leu Glu Glu Lys
            180                 185                 190

Asp His Ile His Arg Val Leu Asp Lys Ile Thr Asp Thr Leu Ile His
            195                 200                 205

Leu Met Ala Lys Ala Gly Leu Thr Leu Gln Gln Gln His Gln Arg Leu
210                 215                 220

Ala Gln Leu Leu Leu Ile Leu Ser His Ile Arg His Met Ser Asn Lys
225                 230                 235                 240

Gly Met Glu His Leu Tyr Ser Met Lys Cys Lys Asn Val Val Pro Leu
                245                 250                 255

Tyr Asp Leu Leu Leu Glu Met Leu Asp Ala His Arg Leu His Ala Pro
            260                 265                 270

Thr Ser Arg Gly Gly Ala Ser Val Glu Glu Thr Asp Gln Ser His Leu
        275                 280                 285

Ala Thr Ala Gly Ser Thr Ser Ser His Ser Leu Gln Lys Tyr Tyr Ile
```

```
                290             295             300
Thr Gly Glu Ala Glu Gly Phe Pro Ala Thr Val
305                 310             315

<210> SEQ ID NO 3
<211> LENGTH: 595
<212> TYPE: PRT
<213> ORGANISM: Homo Sapien

<400> SEQUENCE: 3

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
```

```
                355                 360                 365
Asp Leu Thr Leu His Asp Gln Val His Leu Glu Cys Ala Trp Leu
370                 375                 380
Glu Ile Leu Met Ile Gly Leu Val Trp Arg Ser Met Glu His Pro Val
385                 390                 395                 400
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
                420                 425                 430
Ser Arg Phe Arg Met Met Asn Leu Gln Gly Glu Glu Phe Val Cys Leu
            435                 440                 445
Lys Ser Ile Ile Leu Leu Asn Ser Gly Val Tyr Thr Phe Leu Ser Ser
    450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Gln Arg Leu Ala Gln Leu Leu Leu Ile Leu Ser
                500                 505                 510
His Ile Arg His Met Ser Asn Lys Gly Met Glu His Leu Tyr Ser Met
            515                 520                 525
Lys Cys Lys Asn Val Val Pro Leu Tyr Asp Leu Leu Leu Glu Met Leu
    530                 535                 540
Asp Ala His Arg Leu His Ala Pro Thr Ser Arg Gly Gly Ala Ser Val
545                 550                 555                 560
Glu Glu Thr Asp Gln Ser His Leu Ala Thr Ala Gly Ser Thr Ser Ser
                565                 570                 575
His Ser Leu Gln Lys Tyr Tyr Ile Thr Gly Glu Ala Glu Gly Phe Pro
                580                 585                 590
Ala Thr Val
        595

<210> SEQ ID NO 4
<211> LENGTH: 269
<212> TYPE: PRT
<213> ORGANISM: Mouse

<400> SEQUENCE: 4

Arg Asn Glu Met Gly Ala Ser Gly Asp Met Arg Ala Ala Asn Leu Trp
1               5                   10                  15
Pro Ser Pro Leu Val Ile Lys His Thr Lys Lys Asn Ser Pro Ala Leu
                20                  25                  30
Ser Leu Thr Ala Asp Gln Met Val Ser Ala Leu Leu Asp Ala Glu Pro
            35                  40                  45
Pro Met Ile Tyr Ser Glu Tyr Asp Pro Ser Arg Pro Phe Ser Glu Ala
        50                  55                  60
Ser Met Met Gly Leu Leu Thr Asn Leu Ala Asp Arg Glu Leu Val His
65                  70                  75                  80
Met Ile Asn Trp Ala Lys Arg Val Pro Gly Phe Gly Asp Leu Asn Leu
                85                  90                  95
His Asp Gln Val His Leu Leu Glu Cys Ala Trp Leu Glu Ile Leu Met
                100                 105                 110
Ile Gly Leu Val Trp Arg Ser Met Glu His Pro Gly Lys Leu Leu Phe
            115                 120                 125
Ala Pro Asn Leu Leu Leu Asp Arg Asn Gln Gly Lys Cys Val Glu Gly
```

```
        130                 135                 140
Met Val Glu Ile Phe Asp Met Leu Leu Ala Thr Ser Ser Arg Phe Arg
145                 150                 155                 160

Met Met Asn Leu Gln Gly Glu Glu Phe Val Cys Leu Lys Ser Ile Ile
                165                 170                 175

Leu Leu Asn Ser Gly Val Tyr Thr Phe Leu Ser Ser Thr Leu Lys Ser
                180                 185                 190

Leu Glu Glu Lys Asp His Ile His Arg Val Leu Asp Lys Ile Thr Asp
                195                 200                 205

Thr Leu Ile His Leu Met Ala Lys Ala Gly Leu Thr Leu Gln Gln Gln
                210                 215                 220

His Arg Arg Leu Ala Gln Leu Leu Ile Leu Ser His Ile Arg His
225                 230                 235                 240

Met Ser Asn Lys Gly Met Glu His Leu Tyr Asn Met Lys Cys Lys Asn
                245                 250                 255

Val Val Pro Leu Tyr Asp Leu Leu Leu Glu Met Leu Asp
                260                 265
```

<210> SEQ ID NO 5
<211> LENGTH: 319
<212> TYPE: PRT
<213> ORGANISM: Mouse

<400> SEQUENCE: 5

```
Arg Asn Glu Met Gly Ala Ser Gly Asp Met Arg Ala Ala Asn Leu Trp
1               5                   10                  15

Pro Ser Pro Leu Val Ile Lys His Thr Lys Lys Asn Ser Pro Ala Leu
                20                  25                  30

Ser Leu Thr Ala Asp Gln Met Val Ser Ala Leu Leu Asp Ala Glu Pro
                35                  40                  45

Pro Met Ile Tyr Ser Glu Tyr Asp Pro Ser Arg Pro Phe Ser Glu Ala
                50                  55                  60

Ser Met Met Gly Leu Leu Thr Asn Leu Ala Asp Arg Glu Leu Val His
65                  70                  75                  80

Met Ile Asn Trp Ala Lys Arg Val Pro Gly Phe Gly Asp Leu Asn Leu
                85                  90                  95

His Asp Gln Val His Leu Leu Glu Cys Ala Trp Leu Glu Ile Leu Met
                100                 105                 110

Ile Gly Leu Val Trp Arg Ser Met Glu His Pro Gly Lys Leu Leu Phe
                115                 120                 125

Ala Pro Asn Leu Leu Leu Asp Arg Asn Gln Gly Lys Cys Val Glu Gly
                130                 135                 140

Met Val Glu Ile Phe Asp Met Leu Leu Ala Thr Ser Ser Arg Phe Arg
145                 150                 155                 160

Met Met Asn Leu Gln Gly Glu Glu Phe Val Cys Leu Lys Ser Ile Ile
                165                 170                 175

Leu Leu Asn Ser Gly Val Tyr Thr Phe Leu Ser Ser Thr Leu Lys Ser
                180                 185                 190

Leu Glu Glu Lys Asp His Ile His Arg Val Leu Asp Lys Ile Thr Asp
                195                 200                 205

Thr Leu Ile His Leu Met Ala Lys Ala Gly Leu Thr Leu Gln Gln Gln
                210                 215                 220

His Arg Arg Leu Ala Gln Leu Leu Leu Ile Leu Ser His Ile Arg His
225                 230                 235                 240

Met Ser Asn Lys Gly Met Glu His Leu Tyr Asn Met Lys Cys Lys Asn
```

```
            245                 250                 255
Val Val Pro Leu Tyr Asp Leu Leu Glu Met Leu Asp Ala His Arg
                260                 265                 270

Leu His Ala Pro Ala Ser Arg Met Gly Val Pro Pro Glu Glu Pro Ser
            275                 280                 285

Gln Thr Gln Leu Ala Thr Thr Ser Ser Thr Ser Ala His Ser Leu Gln
        290                 295                 300

Thr Tyr Tyr Ile Pro Pro Glu Ala Glu Gly Phe Pro Asn Thr Ile
305                 310                 315

<210> SEQ ID NO 6
<211> LENGTH: 599
<212> TYPE: PRT
<213> ORGANISM: Mouse

<400> SEQUENCE: 6

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Met Pro Met Glu Arg Ala Leu Gly Glu Val Tyr Val Asp Asn Ser Lys
        35                  40                  45

Pro Thr Val Phe Asn Tyr Pro Glu Gly Ala Ala Tyr Glu Phe Asn Ala
    50                  55                  60

Ala Ala Ala Ala Ala Ala Ala Ser Ala Pro Val Tyr Gly Gln Ser
65                  70                  75                  80

Gly Ile Ala Tyr Gly Pro Gly Ser Glu Ala Ala Phe Ser Ala Asn
            85                  90                  95

Ser Leu Gly Ala Phe Pro Gln Leu Asn Ser Val Ser Pro Ser Pro Leu
        100                 105                 110

Met Leu Leu His Pro Pro Gln Leu Ser Pro Phe Leu His Pro His
    115                 120                 125

Gly Gln Gln Val Pro Tyr Tyr Leu Glu Asn Glu Pro Ser Ala Tyr Ala
130                 135                 140

Val Arg Asp Thr Gly Pro Pro Ala Phe Tyr Arg Ser Asn Ser Asp Asn
145                 150                 155                 160

Arg Arg Gln Asn Gly Arg Glu Arg Leu Ser Ser Ser Asn Glu Lys Gly
                165                 170                 175

Asn Met Ile Met Glu Ser Ala Lys Glu Thr Arg Tyr Cys Ala Val Cys
            180                 185                 190

Asn Asp Tyr Ala Ser Gly Tyr His Tyr Gly Val Trp Ser Cys Glu Gly
        195                 200                 205

Cys Lys Ala Phe Phe Lys Arg Ser Ile Gln Gly His Asn Asp Tyr Met
    210                 215                 220

Cys Pro Ala Thr Asn Gln Cys Thr Ile Asp Lys Asn Arg Arg Lys Ser
225                 230                 235                 240

Cys Gln Ala Cys Arg Leu Arg Lys Cys Tyr Glu Val Gly Met Met Lys
                245                 250                 255

Gly Gly Ile Arg Lys Asp Arg Arg Gly Gly Arg Met Leu Lys His Lys
            260                 265                 270

Arg Gln Arg Asp Asp Leu Glu Gly Arg Asn Glu Met Gly Ala Ser Gly
        275                 280                 285

Asp Met Arg Ala Ala Asn Leu Trp Pro Ser Pro Leu Val Ile Lys His
    290                 295                 300

Thr Lys Lys Asn Ser Pro Ala Leu Ser Leu Thr Ala Asp Gln Met Val
```

```
                305                 310                 315                 320
Ser Ala Leu Leu Asp Ala Glu Pro Pro Met Ile Tyr Ser Glu Tyr Asp
                    325                 330                 335
Pro Ser Arg Pro Phe Ser Glu Ala Ser Met Met Gly Leu Leu Thr Asn
            340                 345                 350
Leu Ala Asp Arg Glu Leu Val His Met Ile Asn Trp Ala Lys Arg Val
        355                 360                 365
Pro Gly Phe Gly Asp Leu Asn Leu His Asp Gln Val His Leu Leu Glu
    370                 375                 380
Cys Ala Trp Leu Glu Ile Leu Met Ile Gly Leu Val Trp Arg Ser Met
385                 390                 395                 400
Glu His Pro Gly Lys Leu Leu Phe Ala Pro Asn Leu Leu Leu Asp Arg
                405                 410                 415
Asn Gln Gly Lys Cys Val Glu Gly Met Val Glu Ile Phe Asp Met Leu
            420                 425                 430
Leu Ala Thr Ser Ser Arg Phe Arg Met Met Asn Leu Gln Gly Glu Glu
        435                 440                 445
Phe Val Cys Leu Lys Ser Ile Ile Leu Leu Asn Ser Gly Val Tyr Thr
    450                 455                 460
Phe Leu Ser Ser Thr Leu Lys Ser Leu Glu Glu Lys Asp His Ile His
465                 470                 475                 480
Arg Val Leu Asp Lys Ile Thr Asp Thr Leu Ile His Leu Met Ala Lys
                485                 490                 495
Ala Gly Leu Thr Leu Gln Gln Gln His Arg Arg Leu Ala Gln Leu Leu
            500                 505                 510
Leu Ile Leu Ser His Ile Arg His Met Ser Asn Lys Gly Met Glu His
        515                 520                 525
Leu Tyr Asn Met Lys Cys Lys Asn Val Val Pro Leu Tyr Asp Leu Leu
    530                 535                 540
Leu Glu Met Leu Asp Ala His Arg Leu His Ala Pro Ala Ser Arg Met
545                 550                 555                 560
Gly Val Pro Pro Glu Glu Pro Ser Gln Thr Gln Leu Ala Thr Thr Ser
                565                 570                 575
Ser Thr Ser Ala His Ser Leu Gln Thr Tyr Tyr Ile Pro Pro Glu Ala
            580                 585                 590
Glu Gly Phe Pro Asn Thr Ile
        595

<210> SEQ ID NO 7
<211> LENGTH: 936
<212> TYPE: DNA
<213> ORGANISM: Artificial Sequence
<220> FEATURE:
<223> OTHER INFORMATION: Renilla Luciferase

<400> SEQUENCE: 7
atggcttcca aggtgtacga ccccgagcaa cgcaaacgca tgatcactgg gcctcagtgg      60
tgggctcgct gcaagcaaat gaacgtgctg gactccttca tcaactacta tgattccgag     120
aagcacgccg agaacgccgt gattttctg catggtaacg ctgcctccag ctacctgtgg     180
aggcacgtcg tgcctcacat cgagcccgtg gctagatgca tcatccctga tctgatcgga     240
atgggtaagt ccggcaagag cgggaatggc tcatatcgcc tcctggatca ctacaagtac     300
ctcaccgctt ggttcgagct gctgaacctt ccaaagaaaa tcatctttgt gggccacgac     360 tgggggggctt gtctggcctt tcactactcc tacgagcacc aagacaagat caaggccatc     420
```

```
gtccatgctg agagtgtcgt ggacgtgatc gagtcctggg acgagtggcc tgacatcgag    480
gaggatatcg ccctgatcaa gagcgaagag ggcgagaaaa tggtgcttga gaataacttc    540
ttcgtcgaga ccatgctccc aagcaagatc atgcggaaac tggagcctga ggagttcgct    600
gcctacctgg agccattcaa ggagaagggc gaggttagac ggcctaccct ctcctggcct    660
cgcgagatcc ctctcgttaa gggaggcaag cccgacgtcg tccagattgt ccgcaactac    720
aacgcctacc ttcgggccag cgacgatctg cctaagatgt tcatcgagtc cgaccctggg    780
ttcttttcca acgctattgt cgagggagct aagaagttcc ctaacaccga gttcgtgaag    840
gtgaagggcc tccacttcag ccaggaggac gctccagatg aaatgggtaa gtacatcaag    900
agcttcgtgg agcgcgtgct gaagaacgag cagtaa                              936
```

<210> SEQ ID NO 8
<211> LENGTH: 311
<212> TYPE: PRT
<213> ORGANISM: Artificial Sequence
<220> FEATURE:
<223> OTHER INFORMATION: Renilla Luciferase

<400> SEQUENCE: 8

```
Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
```

275                 280                 285
Glu Asp Ala Pro Asp Glu Met Gly Lys Tyr Ile Lys Ser Phe Val Glu
            290                 295                 300

Arg Val Leu Lys Asn Glu Gln
305                 310

<210> SEQ ID NO 9
<211> LENGTH: 1629
<212> TYPE: DNA
<213> ORGANISM: Artificial Sequence
<220> FEATURE:
<223> OTHER INFORMATION: Nucleotide Sequence of Coleoptera Luciferase

<400> SEQUENCE: 9

| | | | |
|---|---|---|---|
| atggtaaagc gtgagaaaaa tgtcatctat ggccctgagc ctctccatcc tttggaggat | | | 60 |
| ttgactgccg gcgaaatgct gtttcgtgct ctccgcaagc actctcattt gcctcaagcc | | | 120 |
| ttggtcgatg tggtcggcga tgaatctttg agctacaagg agttttttga ggcaaccgtc | | | 180 |
| ttgctggctc agtccctcca caattgtggc tacaagatga cgacgtcgt tagtatctgt | | | 240 |
| gctgaaaaca atacccgttt cttcattcca gtcatcgccg catggtatat cggtatgatc | | | 300 |
| gtggctccag tcaacgagag ctacattccc gacgaactgt gtaaagtcat gggtatctct | | | 360 |
| aagccacaga ttgtcttcac cactaagaat attctgaaca agtcctgga agtccaaagc | | | 420 |
| cgcaccaact ttattaagcg tatcatcatc ttggacactg tggagaatat tcacggttgc | | | 480 |
| gaatctttgc ctaatttcat ctctcgctat tcagacggca acatcgcaaa ctttaaacca | | | 540 |
| ctccacttcg accctgtgga acaagttgca gccattctgt gtagcagcgg tactactgga | | | 600 |
| ctcccaaagg gagtcatgca gacccatcaa aacatttgcg tgcgtctgat ccatgctctc | | | 660 |
| gatccacgct acggcactca gctgattcct ggtgtcaccg tcttggtcta cttgcctttc | | | 720 |
| ttccatgctt tcggctttca tattactttg ggttacttta tggtcggtct ccgcgtgatt | | | 780 |
| atgttccgcc gttttgatca ggaggctttc ttgaaagcca tccaagatta tgaagtccgc | | | 840 |
| agtgtcatca acgtgcctag cgtgatcctg tttttgtcta agagcccact cgtggacaag | | | 900 |
| tacgacttgt cttcactgcg tgaattgtgt gcggtgccg ctccactggc taaggaggtc | | | 960 |
| gctgaagtgg ccgccaaacg cttgaatctt ccagggattc gttgtggctt cggcctcacc | | | 1020 |
| gaatctacca gtgcgattat ccagactctc ggggatgagt ttaagagcgg ctctttgggc | | | 1080 |
| cgtgtcactc cactcatggc tgctaagatc gctgatcgcg aaactggtaa ggctttgggc | | | 1140 |
| ccgaaccaag tgggcgagct gtgtatcaaa ggccctatgg tgagcaaggg ttatgtcaat | | | 1200 |
| aacgttgaag ctaccaagga ggccatcgac gacgacggct ggttgcattc tggtgatttt | | | 1260 |
| ggatattacg acgaagatga gcattttttac gtcgtggatc gttacaagga gctgatcaaa | | | 1320 |
| tacaagggta gccaggttgc tccagctgag ttggaggaga ttctgttgaa aaatccatgc | | | 1380 |
| attcgcgatg tcgctgtggt cggcattcct gatctggagg ccggcgaact gcttctgct | | | 1440 |
| ttcgttgtca agcagcctgg tacagaaatt accgccaaag aagtgtatga ttacctggct | | | 1500 |
| gaacgtgtga gccatactaa gtacttgcgt ggcggcgtgc gttttgttga ctccatccct | | | 1560 |
| cgtaacgtaa caggcaaaat tacccgcaag gagctgttga acaattgtt ggtgaaggcc | | | 1620 |
| ggcggttag | | | 1629 |

<210> SEQ ID NO 10
<211> LENGTH: 542
<212> TYPE: PRT
<213> ORGANISM: Artificial Sequence
<220> FEATURE:

-continued

<223> OTHER INFORMATION: Amino acid sequence of Coleoptera Luciferase

<400> SEQUENCE: 10

```
Met Val Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Tyr
    210                 215                 220

Gly Thr Gln Leu Ile Pro Gly Val Thr Val Leu Val Tyr Leu Pro Phe
225                 230                 235                 240

Phe His Ala Phe Gly Phe His Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Ile Ile Gln Thr Leu Gly Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
    370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Asp Gly Trp Leu His
```

```
                        405                 410                 415
Ser Gly Asp Phe Gly Tyr Tyr Asp Glu Asp Glu His Phe Tyr Val Val
                420                 425                 430

Asp Arg Tyr Lys Glu Leu Ile Lys Tyr Lys Gly Ser Gln Val Ala Pro
        435                 440                 445

Ala Glu Leu Glu Glu Ile Leu Leu Lys Asn Pro Cys Ile Arg Asp Val
    450                 455                 460

Ala Val Val Gly Ile Pro Asp Leu Glu Ala Gly Glu Leu Pro Ser Ala
465                 470                 475                 480

Phe Val Val Lys Gln Pro Gly Thr Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Val Lys Ala Gly Gly
    530                 535                 540

<210> SEQ ID NO 11
<211> LENGTH: 1653
<212> TYPE: DNA
<213> ORGANISM: Artificial Sequence
<220> FEATURE:
<223> OTHER INFORMATION: Nucleotide sequence of full length Firefly
      Luciferase

<400> SEQUENCE: 11
atggaagacg ccaaaaacat aaagaaaggc ccggcgccat tctatccgct ggaagatgga      60
accgctggag agcaactgca taaggctatg aagagatacg ccctggttcc tggaacaatt     120
gcttttacag atgcacatat cgaggtggac atcacttacg ctgagtactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgggcatt     360
tcgcagccta ccgtggtgtt cgtttccaaa aagggggttgc aaaaaatttt gaacgtgcaa     420
aaaaagctcc caatcatcca aaaaattatt atcatggatt ctaaaacgga ttaccaggga     480
tttcagtcga tgtacacgtt cgtcacatct catctacctc ccggttttaa tgaatacgat     540
tttgtgccag agtccttcga tagggacaag acaattgcac tgatcatgaa ctcctctgga     600
tctactggtc tgcctaaagg tgtcgctctg cctcatagaa ctgcctgcgt gagattctcg     660
catgccagag atcctatttt tggcaatcaa atcattccgg atactgcgat tttaagtgtt     720
gttccattcc atcacggttt tggaatgttt actacactcg gatatttgat atgtggattt     780
cgagtcgtct taatgtatag atttgaagaa gagctgtttc tgaggagcct tcaggattac     840
aagattcaaa gtgcgctgct ggtgccaacc ctattctcct tcttcgccaa agcactctg      900 attgacaaat acgatttatc taatttacac gaaattgctt ctggtggcgc tcccctctct     960
aaggaagtcg gggaagcggt tgccaagagg ttccatctgc caggtatcag gcaaggatat    1020
gggctcactg agactacatc agctattctg attacacccg agggggatga taaaccgggc    1080
gcggtcggta aagttgttcc attttttgaa gcgaaggttg tggatctgga taccgggaaa    1140
acgctgggcg ttaatcaaag aggcgaactg tgtgtgagag gtcctatgat tatgtccggt    1200
tatgtaaaca atccggaagc gaccaacgcc ttgattgaca aggatggatg gctacattct    1260
ggagacatag cttactggga cgaagacgaa cacttcttca tcgttgaccg cctgaagtct    1320
```

```
ctgattaagt acaaaggcta tcaggtggct cccgctgaat tggaatccat cttgctccaa    1380 cacccccaaca tcttcgacgc aggtgtcgca ggtcttcccg acgatgacgc cggtgaactt    1440
cccgccgccg ttgttgtttt ggagcacgga aagacgatga cggaaaaaga gatcgtggat    1500
tacgtcgcca gtcaagtaac aaccgcgaaa aagttgcgcg gaggagttgt gtttgtggac    1560
gaagtaccga aaggtcttac cggaaaactc gacgcaagaa aaatcagaga gatcctcata    1620
aaggccaaga agggcggaaa gatcgccgtg taa                                 1653
```

<210> SEQ ID NO 12
<211> LENGTH: 550
<212> TYPE: PRT
<213> ORGANISM: Artificial Sequence
<220> FEATURE:
<223> OTHER INFORMATION: Full Length Firefly Luciferase amino acid

<400> SEQUENCE: 12

```
Met Glu Asp Ala Lys Asn Ile Lys Lys Gly Pro Ala Pro Phe Tyr Pro
 1               5                  10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300
```

```
Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
530                 535                 540

Gly Gly Lys Ile Ala Val
545                 550

<210> SEQ ID NO 13
<211> LENGTH: 444
<212> TYPE: DNA
<213> ORGANISM: Artificial Sequence
<220> FEATURE:
<223> OTHER INFORMATION: DNA binding domain polynucleotide sequence

<400> SEQUENCE: 13
atgaagctac tgtcttctat cgaacaagca tgcgatattt gccgacttaa aaagctcaag      60
tgctccaaag aaaaaccgaa gtgcgccaag tgtctgaaga caactgggag tgtcgctac     120 tctcccaaaa ccaaaaggtc tccgctgact agggcacatc tgacagaagt ggaatcaagg     180
ctagaaagac tggaacagct atttctactg attttttcctc gagaagacct tgacatgatt    240
ttgaaaatgg attctttaca ggatataaaa gcattgttaa caggattatt tgtacaagat     300
aatgtgaata agatgccgt cacagataga ttggcttcag tggagactga tatgcctcta      360
acattgagac agcatagaat aagtgcgaca tcatcatcgg aagagagtag taacaaaggt      420
caaagacagt tgactgtatc gccg                                             444

<210> SEQ ID NO 14
<211> LENGTH: 148
<212> TYPE: PRT
<213> ORGANISM: Artificial Sequence
<220> FEATURE:
```

<223> OTHER INFORMATION: DNA binding domain protein sequence

<400> SEQUENCE: 14

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Asn Lys Gly Gln Arg Gln Leu
    130                 135                 140

Thr Val Ser Pro
145

<210> SEQ ID NO 15
<211> LENGTH: 135
<212> TYPE: DNA
<213> ORGANISM: Artificial Sequence
<220> FEATURE:
<223> OTHER INFORMATION: Transactivation domain polynucleotide sequence

<400> SEQUENCE: 15
gcccccccga ccgatgtcag cctgggggac gagctccact tagacggcga ggacgtggcg      60
atggcgcatg ccgacgcgct agacgatttc gatctggaca tgttggggga cggggattcc     120
ccgggtccga gatcc                                                      135

<210> SEQ ID NO 16
<211> LENGTH: 45
<212> TYPE: PRT
<213> ORGANISM: Artificial Sequence
<220> FEATURE:
<223> OTHER INFORMATION: VP16 Transactivation domain protein sequence

<400> SEQUENCE: 16

Ala Pro Pro Thr Asp Val Ser Leu Gly Asp Glu Leu His Leu Asp Gly
1               5                   10                  15

Glu Asp Val Ala Met Ala His Ala Asp Ala Leu Asp Asp Phe Asp Leu
            20                  25                  30

Asp Met Leu Gly Asp Gly Asp Ser Pro Gly Pro Arg Ser
        35                  40                  45

<210> SEQ ID NO 17
<211> LENGTH: 191
<212> TYPE: DNA
<213> ORGANISM: Artificial Sequence
<220> FEATURE:
<223> OTHER INFORMATION: DNA binding sequence

<400> SEQUENCE: 17
ggactgggga tcctctagag tggtaccgag ctcatttagg tgacactata gaatacaagc      60

```
ttgcatgcct gcaggtccgg aggacagtac tccgctcgga ggacagtact ccgctcggag    120
gacagtactc cgctcggagg acagtactcc gctcggagga cagtactccg actctagagg    180
atccccagtc c                                                         191

<210> SEQ ID NO 18
<211> LENGTH: 77
<212> TYPE: DNA
<213> ORGANISM: Artificial Sequence
<220> FEATURE:
<223> OTHER INFORMATION: E4 minimal promoter

<400> SEQUENCE: 18
cgagacacca ctcgacacgg caccagctca atcagtcaca gtgtaaaaaa gggccaagtg     60
cagagcgagt atatata                                                   77

<210> SEQ ID NO 19
<211> LENGTH: 732
<212> TYPE: DNA
<213> ORGANISM: Artificial Sequence
<220> FEATURE:
<223> OTHER INFORMATION: Green Fluorescent Protein

<400> SEQUENCE: 19
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctgggcac    420 aagctggagt acaactacaa cagccacaac gtctatatca tggccgacta ttgtctaagc    480
ttctgtaaga acggcatcaa ggtgaacttc aagatccgcc acaacatcga ggacggcagc    540
gtgcagctcg ccgaccacta ccagcagaac ccccccatcg gcgacggccc cgtgctgctg    600
cccgacaacc actacctgag cacccagtcc gccctgagca agacccccaa cgagaagcgc    660
gatcacatgg tcctgctgga gttcgtgacc gccgcgggga tcactctcgg catggacgag    720
ctgtacaagt aa                                                        732

<210> SEQ ID NO 20
<211> LENGTH: 678
<212> TYPE: DNA
<213> ORGANISM: Artificial Sequence
<220> FEATURE:
<223> OTHER INFORMATION: Red Fluorescent Protein

<400> SEQUENCE: 20
atgaggtctt ccaagaatgt tatcaaggag ttcatgaggt ttaaggttcg catggaagga     60
acggtcaatg ggcacgagtt tgaaatagaa ggcgaaggag aggggaggcc atacgaaggc    120
cacaataccg taaagcttaa ggtaaccaag gggggacctt tgccatttgc ttgggatatt    180
ttgtcaccac aatttcagta tggaagcaag gtatatgtca agcaccctgc cgacatacca    240
gactataaaa agctgtcatt tcctgaagga tttaaatggg aaagggtcat gaactttgaa    300
gacggtggcg tcgttactgt aacccaggat tccagtttgc aggatggctg tttcatctac    360
aaggtcaagt tcattggcgt gaactttcct tccgatggac ctgttatgca aaagaagaca    420
```

| | |
|---|---|
| atgggctggg aagccagcac tgagcgtttg tatcctcgtg atggcgtgtt gaaaggagag | 480 |
| attcataagg ctctgaagct gaaagacggt ggtcattacc tagttgaatt caaaagtatt | 540 |
| tacatggcaa agaagcctgt gcagctacca gggtactact atgttgactc caaactggat | 600 |
| ataacaagcc acaacgaaga ctatacaatc gttgagcagt atgaaagaac cgagggacgc | 660 |
| caccatctgt tcctttag | 678 |

<210> SEQ ID NO 21
<211> LENGTH: 3051
<212> TYPE: DNA
<213> ORGANISM: Artificial Sequence
<220> FEATURE:
<223> OTHER INFORMATION: B-galactosidase

<400> SEQUENCE: 21

| | |
|---|---|
| atggtcgttt tacaacgtcg tgactgggaa aaccctggcg ttacccaact taatcgcctt | 60 |
| gcagcacatc cccctttcgc cagctggcgt aatagcgaag aggcccgcac cgatcgccct | 120 |
| tcccaacagt tgcgcagcct gaatggcgaa tggcgctttg cctggtttcc ggcaccagaa | 180 |
| gcggtgccgg aaagctggct ggagtgcgat cttcctgagg ccgatactgt cgtcgtcccc | 240 |
| tcaaactggc agatgcacgg ttacgatgcg cccatctaca ccaacgtgac ctatcccatt | 300 |
| acggtcaatc cgccgtttgt tcccacggag aatccgacgg gttgttactc gctcacattt | 360 |
| aatgttgatg aaagctggct acaggaaggc cagacgcgaa ttattttga tggcgttaac | 420 |
| tcggcgtttc atctgtggtg caacgggcgc tgggtcggtt acggccagga cagtcgtttg | 480 |
| ccgtctgaat ttgacctgag cgcattttta cgcgccggag aaaaccgcct cgcggtgatg | 540 |
| gtgctgcgct ggagtgacgg cagttatctg gaagatcagg atatgtggcg gatgagcggc | 600 |
| attttccgtg acgtctcgtt gctgcataaa ccgactacac aaatcagcga tttccatgtt | 660 |
| gccactcgct ttaatgatga tttcagccgc gctgtactgg aggctgaagt tcagatgtgc | 720 |
| ggcgagttgc gtgactacct acgggtaaca gtttctttat ggcagggtga acgcaggtc | 780 |
| gccagcggca ccgcgccttt cggcggtgaa attatcgatg agcgtggtgg ttatgccgat | 840 |
| cgcgtcacac tacgtctgaa cgtcgaaaac ccgaaactgt ggagcgccga atcccgaat | 900 |
| ctctatcgtg cggtggttga actgcacacc gccgacggca cgctgattga agcagaagcc | 960 |
| tgcgatgtcg gtttccgcga ggtgcggatt gaaaatggtc tgctgctgct gaacggcaag | 1020 |
| ccgttgctga ttcgaggcgt taaccgtcac gagcatcatc ctctgcatgg tcaggtcatg | 1080 |
| gatgagcaga cgatggtgca ggatatcctg ctgatgaagc agaacaactt taacgccgtg | 1140 |
| cgctgttcgc attatccgaa ccatccgctg tggtacacgc tgtgcgaccg ctacggcctg | 1200 |
| tatgtggtgg atgaagccaa tattgaaacc cacggcatgg tgccaatgaa tcgtctgacc | 1260 |
| gatgatccgc gctggctacc ggcgatgagc gaacgcgtaa cgcgaatggt gcagcgcgat | 1320 |
| cgtaatcacc cgagtgtgat catctggtcg ctggggaatg aatcaggcca cggcgctaat | 1380 |
| cacgacgcgc tgtatcgctg gatcaaatct gtcgatcctt cccgcccggt gcagtatgaa | 1440 |
| ggcggcggag ccgacaccac ggccaccgat attatttgcc cgatgtacgc gcgcgtggat | 1500 |
| gaagaccagc ccttcccggc tgtgccgaaa tggtccatca aaaaatggct ttcgctacct | 1560 |
| ggagagacgc gcccgctgat cctttgcgaa tacgcccacg cgatgggtaa cagtcttggc | 1620 |
| ggtttcgcta atactgggca ggctttcgt cagtatcccc gtttacaggg cggcttcgtc | 1680 |
| tgggactggg tggatcagtc gctgattaaa tatgatgaaa acggcaaccc gtggtcggct | 1740 |
| tacggcggtg attttggcga tacgccgaac gatcgccagt tctgtatgaa cggtctggtc | 1800 |

| | |
|---|---|
| tttgccgacc gcacgccgca tccagcgctg acggaagcaa acaccagca gcagtttttc | 1860 |
| cagttccgtt tatccgggca aaccatcgaa gtgaccagcg aatacctgtt ccgtcatagc | 1920 |
| gataacgagc tcctgcactg gatggtggcg ctggatggta agccgctggc aagcggtgaa | 1980 |
| gtgcctctgg atgtcgctcc acaaggtaaa cagttgattg aactgcctga actaccgcag | 2040 |
| ccggagagcg ccgggcaact ctggctcaca gtacgcgtag tgcaaccgaa cgcgaccgca | 2100 |
| tggtcagaag ccgggcacat cagcgcctgg cagcagtggc gtctggcgga aaacctcagt | 2160 |
| gtgacgctcc ccgccgcgtc ccacgccatc ccgcatctga ccaccagcga atggattttt | 2220 |
| tgcatcgagc tgggtaataa gcgttggcaa tttaaccgcc agtcaggctt ctttcacag | 2280 |
| atgtggattg gcgataaaaa caactgctg acgccgctgc gcgatcagtt cacccgtgca | 2340 |
| ccgctggata acgacattgg cgtaagtgaa gcgacccgca ttgaccctaa cgcctgggtc | 2400 |
| gaacgctgga aggcggcggg ccattaccag gccgaagcag cgttgttgca gtgcacggca | 2460 |
| gatacacttg ctgatgcggt gctgattacg accgctcacg cgtggcagca tcaggggaaa | 2520 |
| accttattta tcagccggaa aacctaccgg attgatggta gtggtcaaat ggcgattacc | 2580 |
| gttgatgttg aagtggcgag cgatacaccg catccggcgc ggattggcct gaactgccag | 2640 |
| ctggcgcagg tagcagagcg ggtaaactgg ctcggattag gccgcaaga aaactatccc | 2700 |
| gaccgcctta ctgccgcctg ttttgaccgc tgggatctgc cattgtcaga catgtatacc | 2760 |
| ccgtacgtct tcccgagcga aaacggtctg cgctgcggga cgcgcgaatt gaattatggc | 2820 |
| ccacaccagt ggcgcggcga cttccagttc aacatcagcc gctacagtca acagcaactg | 2880 |
| atggaaaacca gccatcgcca tctgctgcac gcggaagaag gcacatggct gaatatcgac | 2940 |
| ggtttccata tggggattgg tggcgacgac tcctggagcc cgtcagtatc ggcggaattc | 3000 |
| cagctgagcg ccggtcgcta ccattaccag ttggtctggt gtcaaaaata a | 3051 |

<210> SEQ ID NO 22
<211> LENGTH: 861
<212> TYPE: DNA
<213> ORGANISM: Artificial Sequence
<220> FEATURE:
<223> OTHER INFORMATION: B-Lactamase

<400> SEQUENCE: 22

| | |
|---|---|
| atgagtattc aacatttccg tgtcgcccct tattccttt ttgcggcatt ttgccttcct | 60 |
| gtttttgctc acccagaaac gctggtgaaa gtaaaagatg ctgaagatca gttgggtgca | 120 |
| cgagtgggtt acatcgaact ggatctcaac agcggtaaga tccttgagag ttttcgcccc | 180 |
| gaagaacgtt ttccaatgat gagcactttt aaagttctgc tatgtggcgc ggtattatcc | 240 |
| cgtattgacg ccgggcaaga gcaactcggt cgccgcatac actattctca gaatgacttg | 300 |
| gttgagtact caccagtcac agaaaagcat cttacggatg gcatgacagt aagagaatta | 360 |
| tgcagtgctg ccataaccat gagtgataac actgcggcca acttacttct gacaacgatc | 420 |
| ggaggaccga aggagctaac cgcttttttg cacaacatgg gggatcatgt aactcgcctt | 480 |
| gatcgttggg aaccggagct gaatgaagcc ataccaaacg acgagcgtga caccacgatg | 540 |
| cctgtagcaa tggcaacaac gttgcgcaaa ctattaactg gcgaactact tactctagct | 600 |
| tcccggcaac aattaataga ctggatggag gcggataaag ttgcaggacc acttctgcgc | 660 |
| tcggcccttc cggctggctg gtttattgct gataaatctg gagccggtga gcgtgggtct | 720 |
| cgcggtatca ttgcagcact ggggccagat ggtaagccct cccgtatcgt agttatctac | 780 |
| acgacgggga gtcaggcaac tatggatgaa cgaaatagac agatcgctga gataggtgcc | 840 | tcactgatta agcattggta a                                                                        861

<210> SEQ ID NO 23
<211> LENGTH: 595
<212> TYPE: PRT
<213> ORGANISM: Homo Sapien

<400> SEQUENCE: 23

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

-continued

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Thr Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 24
<211> LENGTH: 315
<212> TYPE: PRT
<213> ORGANISM: Homo Sapien

<400> SEQUENCE: 24

Gly Ser Ala Gly Asp Met Arg Ala Ala Asn Leu Trp Pro Ser Pro Leu
1               5                   10                  15

Met Ile Lys Arg Ser Lys Lys Asn Ser Leu Ala Leu Ser Leu Thr Ala
            20                  25                  30

Asp Gln Met Val Ser Ala Leu Leu Asp Ala Glu Pro Pro Ile Leu Tyr
        35                  40                  45

Ser Glu Tyr Asp Pro Thr Arg Pro Phe Ser Glu Ala Ser Met Met Gly
    50                  55                  60

Leu Leu Thr Asn Leu Ala Asp Arg Glu Leu Val His Met Ile Asn Trp
65                  70                  75                  80

Ala Lys Arg Val Pro Gly Phe Val Asp Leu Thr Leu His Asp Gln Val
                85                  90                  95

His Leu Leu Glu Cys Ala Trp Leu Glu Ile Leu Met Ile Gly Leu Val
            100                 105                 110

Trp Arg Ser Met Glu His Pro Val Lys Leu Leu Phe Ala Pro Asn Leu
        115                 120                 125

Leu Leu Asp Arg Asn Gln Gly Lys Cys Val Glu Gly Met Val Glu Ile
    130                 135                 140

-continued

```
Phe Asp Met Leu Leu Ala Thr Ser Ser Arg Phe Arg Met Met Asn Leu
145                 150                 155                 160

Gln Gly Glu Glu Phe Val Cys Leu Lys Ser Ile Ile Leu Leu Asn Ser
            165                 170                 175

Gly Val Tyr Thr Phe Leu Ser Ser Thr Leu Lys Ser Leu Glu Glu Lys
        180                 185                 190

Asp His Ile His Arg Val Leu Asp Lys Ile Thr Asp Thr Leu Ile His
    195                 200                 205

Leu Met Ala Lys Ala Gly Leu Thr Leu Gln Gln His Gln Arg Leu
210                 215                 220

Ala Gln Leu Leu Leu Ile Leu Ser His Ile Arg His Met Ser Asn Lys
225                 230                 235                 240

Thr Met Glu His Leu Tyr Ser Met Lys Cys Lys Asn Val Val Pro Leu
            245                 250                 255

Tyr Asp Leu Leu Leu Glu Met Leu Asp Ala His Arg Leu His Ala Pro
        260                 265                 270

Thr Ser Arg Gly Gly Ala Ser Val Glu Glu Thr Asp Gln Ser His Leu
    275                 280                 285

Ala Thr Ala Gly Ser Thr Ser Ser His Ser Leu Gln Lys Tyr Tyr Ile
290                 295                 300

Thr Gly Glu Ala Glu Gly Phe Pro Ala Thr Val
305                 310                 315

<210> SEQ ID NO 25
<211> LENGTH: 315
<212> TYPE: PRT
<213> ORGANISM: Homo Sapien

<400> SEQUENCE: 25

Gly Ser Ala Gly Asp Met Arg Ala Ala Asn Leu Trp Pro Ser Pro Leu
1               5                   10                  15

Met Ile Lys Arg Ser Lys Lys Asn Ser Leu Ala Leu Ser Leu Thr Ala
            20                  25                  30

Asp Gln Met Val Ser Ala Leu Leu Asp Ala Glu Pro Pro Ile Leu Tyr
        35                  40                  45

Ser Glu Tyr Asp Pro Thr Arg Pro Phe Ser Glu Ala Ser Met Met Gly
    50                  55                  60

Leu Leu Thr Asn Leu Ala Asp Arg Glu Leu Val His Met Ile Asn Trp
65                  70                  75                  80

Ala Lys Arg Val Pro Gly Phe Val Asp Leu Thr Leu His Asp Gln Val
            85                  90                  95

His Leu Leu Glu Cys Ala Trp Leu Glu Ile Leu Met Ile Gly Leu Val
        100                 105                 110

Trp Arg Ser Met Glu His Pro Val Lys Leu Leu Phe Ala Pro Asn Leu
    115                 120                 125

Leu Leu Asp Arg Asn Gln Gly Lys Cys Val Glu Gly Met Val Glu Ile
130                 135                 140

Phe Asp Met Leu Leu Ala Thr Ser Ser Arg Phe Arg Met Met Asn Leu
145                 150                 155                 160

Gln Gly Glu Glu Phe Val Cys Leu Lys Ser Ile Ile Leu Leu Asn Ser
            165                 170                 175

Gly Val Tyr Thr Phe Leu Ser Ser Thr Leu Lys Ser Leu Glu Glu Lys
        180                 185                 190

Asp His Ile His Arg Val Leu Asp Lys Ile Thr Asp Thr Leu Ile His
    195                 200                 205
```

```
Leu Met Ala Lys Ala Gly Leu Thr Leu Gln Gln Gln His Gln Arg Leu
    210                 215                 220

Ala Gln Leu Leu Leu Ile Leu Ser His Ile Arg His Met Ser Asn Lys
225                 230                 235                 240

Arg Met Glu His Leu Tyr Ser Met Lys Cys Lys Asn Val Val Pro Leu
                245                 250                 255

Tyr Asp Leu Leu Leu Glu Met Leu Asp Ala His Arg Leu His Ala Pro
                260                 265                 270

Thr Ser Arg Gly Gly Ala Ser Val Glu Glu Thr Asp Gln Ser His Leu
            275                 280                 285

Ala Thr Ala Gly Ser Thr Ser Ser His Ser Leu Gln Lys Tyr Tyr Ile
        290                 295                 300

Thr Gly Glu Ala Glu Gly Phe Pro Ala Thr Val
305                 310                 315

<210> SEQ ID NO 26
<211> LENGTH: 315
<212> TYPE: PRT
<213> ORGANISM: Homo Sapien

<400> SEQUENCE: 26

Gly Ser Ala Gly Asp Met Arg Ala Ala Asn Leu Trp Pro Ser Pro Leu
1               5                   10                  15

Met Ile Lys Arg Ser Lys Lys Asn Ser Leu Ala Leu Ser Leu Thr Ala
                20                  25                  30

Asp Gln Met Val Ser Ala Leu Leu Asp Ala Glu Pro Pro Ile Leu Tyr
            35                  40                  45

Ser Glu Tyr Asp Pro Thr Arg Pro Phe Ser Glu Ala Ser Met Met Gly
50                  55                  60

Leu Leu Thr Asn Leu Ala Asp Arg Glu Leu Val His Met Ile Asn Trp
65                  70                  75                  80

Ala Lys Arg Val Pro Gly Phe Val Asp Leu Thr Leu His Asp Gln Val
                85                  90                  95

His Leu Leu Glu Cys Ala Trp Leu Glu Ile Leu Met Ile Gly Leu Val
            100                 105                 110

Trp Arg Ser Met Glu His Pro Val Lys Leu Leu Phe Ala Pro Asn Leu
        115                 120                 125

Leu Leu Asp Arg Asn Gln Gly Lys Cys Val Glu Gly Met Val Glu Ile
130                 135                 140

Phe Asp Met Leu Leu Ala Thr Ser Ser Arg Phe Arg Met Met Asn Leu
145                 150                 155                 160

Gln Gly Glu Glu Phe Val Cys Leu Lys Ser Ile Ile Leu Leu Asn Ser
                165                 170                 175

Gly Val Tyr Thr Phe Leu Ser Ser Thr Leu Lys Ser Leu Glu Glu Lys
            180                 185                 190

Asp His Ile His Arg Val Leu Asp Lys Ile Thr Asp Thr Leu Ile His
        195                 200                 205

Leu Met Ala Lys Ala Gly Leu Thr Leu Gln Gln Gln His Gln Arg Leu
210                 215                 220

Ala Gln Leu Leu Leu Ile Leu Ser His Ile Arg His Met Ser Asn Lys
225                 230                 235                 240

Val Met Glu His Leu Tyr Ser Met Lys Cys Lys Asn Val Val Pro Leu
                245                 250                 255

Tyr Asp Leu Leu Leu Glu Met Leu Asp Ala His Arg Leu His Ala Pro
            260                 265                 270
```

```
Thr Ser Arg Gly Gly Ala Ser Val Glu Glu Thr Asp Gln Ser His Leu
    275                 280                 285

Ala Thr Ala Gly Ser Thr Ser Ser His Ser Leu Gln Lys Tyr Tyr Ile
290                 295                 300

Thr Gly Glu Ala Glu Gly Phe Pro Ala Thr Val
305                 310                 315

<210> SEQ ID NO 27
<211> LENGTH: 550
<212> TYPE: PRT
<213> ORGANISM: Homo Sapien

<400> SEQUENCE: 27

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
                20                  25                  30

Tyr Ala Leu Val Pro Gly Thr Ile Ala Phe Thr Asp Ala His Ile Glu
            35                  40                  45

Val Asp Ile Thr Tyr Ala Glu Tyr Phe Glu Met Ser Val Arg Leu Ala
50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335
```

```
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
        355                 360                 365
Phe Glu Ala Lys Val Val Asp Leu Asp Thr Gly Lys Thr Leu Gly Val
    370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp His Phe
            420                 425                 430
Phe Ile Val Asp Arg Leu Lys Ser Leu Ile Lys Tyr Lys Gly Tyr Gln
    435                 440                 445
Val Ala Pro Ala Glu Leu Glu Ser Ile Leu Leu Gln His Pro Asn Ile
450                 455                 460
Phe Asp Ala Gly Val Ala Gly Leu Pro Asp Asp Ala Gly Glu Leu
465                 470                 475                 480
Pro Ala Ala Val Val Val Leu Glu His Gly Lys Thr Met Thr Glu Lys
                485                 490                 495
Glu Ile Val Asp Tyr Val Ala Ser Gln Val Thr Thr Ala Lys Lys Leu
            500                 505                 510
Arg Gly Gly Val Val Phe Val Asp Glu Val Pro Lys Gly Leu Thr Gly
        515                 520                 525
Lys Leu Asp Ala Arg Lys Ile Arg Glu Ile Leu Ile Lys Ala Lys Lys
    530                 535                 540
Gly Gly Lys Ile Ala Val
545                 550

<210> SEQ ID NO 28
<211> LENGTH: 558
<212> TYPE: DNA
<213> ORGANISM: Artificial Sequence
<220> FEATURE:
<223> OTHER INFORMATION: Nucleotide sequence of Goussia Luciferase

<400> SEQUENCE: 28
atgggagtga agttctttt tgcccttatt tgtattgctg tggccgaggc caaaccaact      60
gaaaacaatg aagatttcaa cattgtagct gtagctagca actttgctac aacggatctc    120
gatgctgacc gtggtaaatt gcccggaaaa aaattaccac ttgaggtact caagaaaatg    180
gaagccaatg ctaggaaagc tggctgcact aggggatgtc tgatatgcct gtcacacatc    240
aagtgtacac ccaaaatgaa gaagtttatc ccaggaagat gccacaccta tgaaggagac    300
aaagaaagtg cacagggagg aataggagag ctattgttg acattcctga aattcctggg     360
tttaaggatt ggaacccat ggaacaattc attgcacaag ttgacctatg tgtagactgc     420
acaactggat gcctcaaagg tcttgccaat gtgcaatgtt ctgatttact caagaaatgg    480
ctgccacaaa gatgtgcaac ttttgctagc aaaattcaag ccaagtggac aaaataaag    540 ggtgccggtg gtgattaa                                                   558

<210> SEQ ID NO 29
<211> LENGTH: 185
<212> TYPE: PRT
<213> ORGANISM: Artificial Sequence
<220> FEATURE:
<223> OTHER INFORMATION: Amino acid sequence of Goussia Luciferase
```

<400> SEQUENCE: 29

```
Met Gly Val Lys Val Leu Phe Ala Leu Ile Cys Ile Ala Val Ala Glu
1               5                   10                  15
Ala Lys Pro Thr Glu Asn Asn Glu Asp Phe Asn Ile Val Ala Val Ala
            20                  25                  30
Ser Asn Phe Ala Thr Thr Asp Leu Asp Ala Asp Arg Gly Lys Leu Pro
        35                  40                  45
Gly Lys Lys Leu Pro Leu Glu Val Leu Lys Glu Met Glu Ala Asn Ala
50                  55                  60
Arg Lys Ala Gly Cys Thr Arg Gly Cys Leu Ile Cys Leu Ser His Ile
65                  70                  75                  80
Lys Cys Thr Pro Lys Met Lys Lys Phe Ile Pro Gly Arg Cys His Thr
                85                  90                  95
Tyr Glu Gly Asp Lys Glu Ser Ala Gln Gly Gly Ile Gly Glu Ala Ile
            100                 105                 110
Val Asp Ile Pro Glu Ile Pro Gly Phe Lys Asp Leu Glu Pro Met Glu
        115                 120                 125
Gln Phe Ile Ala Gln Val Asp Leu Cys Val Asp Cys Thr Thr Gly Cys
130                 135                 140
Leu Lys Gly Leu Ala Asn Val Gln Cys Ser Asp Leu Leu Lys Lys Trp
145                 150                 155                 160
Leu Pro Gln Arg Cys Ala Thr Phe Ala Ser Lys Ile Gln Gly Gln Val
                165                 170                 175
Asp Lys Ile Lys Gly Ala Gly Gly Asp
            180                 185
```

<210> SEQ ID NO 30
<211> LENGTH: 567
<212> TYPE: DNA
<213> ORGANISM: Artificial Sequence
<220> FEATURE:
<223> OTHER INFORMATION: Nucleotide sequence of Aqueorin Photoprotein
      Luciferase

<400> SEQUENCE: 30

```
atgcttacat cagacttcga caacccaaga tggattggac gacacaagca tatgttcaat      60
ttccttgatg tcaaccacaa tggaaaaatc tctcttgacg agatggtcta caaggcatct     120
gatattgtca tcaataacct tggagcaaca cctgagcaag ccaaacgaca caaagatgct     180
gtagaagcct tcttcggagg agctggaatg aaatatggtg tggaaactga ttggcctgca     240
tatattgaag gatggaaaaa attggctact gatgaattgg agaaatacgc caaaaacgaa     300
ccaacgctca tccgtatatg gggtgatgct tgtttgata tcgttgacaa agatcaaaat     360
ggagccatta cactggatga atggaaagca tacaccaaag ctgctggtat catccaatca     420
tcagaagatt gcgaggaaac attcagagtg tgcgatattg atgaaagtgg acaactcgat     480
gttgatgaga tgacaagaca acatttagga ttttggtaca ccatggatcc tgcttgcgaa     540
aagctctacg gtggagctgt cccctaa                                         567
```

<210> SEQ ID NO 31
<211> LENGTH: 188
<212> TYPE: PRT
<213> ORGANISM: Artificial Sequence
<220> FEATURE:
<223> OTHER INFORMATION: Amino acid sequence of Aqueorin Photoprotein
      Luciferase

<400> SEQUENCE: 31

```
Met Leu Thr Ser Asp Phe Asp Asn Pro Arg Trp Ile Gly Arg His Lys
1               5                   10                  15

His Met Phe Asn Phe Leu Asp Val Asn His Asn Gly Lys Ile Ser Leu
            20                  25                  30

Asp Glu Met Val Tyr Lys Ala Ser Asp Ile Val Ile Asn Asn Leu Gly
        35                  40                  45

Ala Thr Pro Glu Gln Ala Lys Arg His Lys Asp Ala Val Glu Ala Phe
    50                  55                  60

Phe Gly Gly Ala Gly Met Lys Tyr Gly Val Glu Thr Asp Trp Pro Ala
65              70                  75                  80

Tyr Ile Glu Gly Trp Lys Lys Leu Ala Thr Asp Glu Leu Glu Lys Tyr
                85                  90                  95

Ala Lys Asn Glu Pro Thr Leu Ile Arg Ile Trp Gly Asp Ala Leu Phe
            100                 105                 110

Asp Ile Val Asp Lys Asp Gln Asn Gly Ala Ile Thr Leu Asp Glu Trp
        115                 120                 125

Lys Ala Tyr Thr Lys Ala Ala Gly Ile Ile Gln Ser Ser Glu Asp Cys
    130                 135                 140

Glu Glu Thr Phe Arg Val Cys Asp Ile Asp Glu Ser Gly Gln Leu Asp
145             150                 155                 160

Val Asp Glu Met Thr Arg Gln His Leu Gly Phe Trp Tyr Thr Met Asp
                165                 170                 175

Pro Ala Cys Glu Lys Leu Tyr Gly Gly Ala Val Pro
            180                 185
```

<210> SEQ ID NO 32
<211> LENGTH: 691
<212> TYPE: DNA
<213> ORGANISM: Artificial Sequence
<220> FEATURE:
<223> OTHER INFORMATION: Nucleotide sequence of Bacterial Luciferase

<400> SEQUENCE: 32

```
atgaataaat ggaattacgg agtcttcttc gttaactttt ataataaagg ccaacaagag     60
ccatcaaaaa cgatgaataa tgcattagaa acattacgta ttattgatga agatacatct    120
atttatgatg tgattaatat tgatgaccac tatcttgtaa agaaagacag tgaagataaa    180
aagctagcgt cttttattac actaggagaa aaactatatg tgcttgctac cagtgaaaac    240
acagttgata ttgcagcgaa atatgcatta ccgttagttt tcaaatggga tgatataaat    300
gaggaacgac ttaaattgtt gagtttttat aatgcatccg caagtaaata taacaagaat    360
atagatttgg ttcgacacca gcttatgtta catgtcaatg ttaatgaggc agaaactgta    420
gcaaaagaag aactcaaatt atatattgaa aactatgtag catgtacaca gcctagtaat    480
tttaatggct cgattgatag tattattcag agtaacgtga cagggagtta taagactgt     540
ttgtcatatg tagcgaatct tgctggtaaa tttgataata ctgtggactt cttactttgt    600
tttgagtcaa tgcaagatca aaataagaaa aaatcagtaa tgatagatct taataatcaa    660
gttattaagt tccgccaaga taataatcta a                                   691
```

<210> SEQ ID NO 33
<211> LENGTH: 231
<212> TYPE: PRT
<213> ORGANISM: Artificial Sequence
<220> FEATURE:
<223> OTHER INFORMATION: Amino acid sequence of Bacterial Luciferase
<220> FEATURE:
<221> NAME/KEY: misc_feature
<222> LOCATION: (231)..(231)

<223> OTHER INFORMATION: Xaa can be any naturally occurring amino acid

<400> SEQUENCE: 33

Met Asn Lys Trp Asn Tyr Gly Val Phe Phe Val Asn Phe Tyr Asn Lys
1               5                   10                  15

Gly Gln Gln Glu Pro Ser Lys Thr Met Asn Asn Ala Leu Glu Thr Leu
            20                  25                  30

Arg Ile Ile Asp Glu Asp Thr Ser Ile Tyr Asp Val Ile Asn Ile Asp
        35                  40                  45

Asp His Tyr Leu Val Lys Lys Asp Ser Glu Asp Lys Lys Leu Ala Ser
    50                  55                  60

Phe Ile Thr Leu Gly Glu Lys Leu Tyr Val Leu Ala Thr Ser Glu Asn
65                  70                  75                  80

Thr Val Asp Ile Ala Ala Lys Tyr Ala Leu Pro Leu Val Phe Lys Trp
                85                  90                  95

Asp Asp Ile Asn Glu Glu Arg Leu Lys Leu Leu Ser Phe Tyr Asn Ala
            100                 105                 110

Ser Ala Ser Lys Tyr Asn Lys Asn Ile Asp Leu Val Arg His Gln Leu
        115                 120                 125

Met Leu His Val Asn Val Asn Glu Ala Glu Thr Val Ala Lys Glu Glu
    130                 135                 140

Leu Lys Leu Tyr Ile Glu Asn Tyr Val Ala Cys Thr Gln Pro Ser Asn
145                 150                 155                 160

Phe Asn Gly Ser Ile Asp Ser Ile Ile Gln Ser Asn Val Thr Gly Ser
                165                 170                 175

Tyr Lys Asp Cys Leu Ser Tyr Val Ala Asn Leu Ala Gly Lys Phe Asp
            180                 185                 190

Asn Thr Val Asp Phe Leu Leu Cys Phe Glu Ser Met Gln Asp Gln Asn
        195                 200                 205

Lys Lys Lys Ser Val Met Ile Asp Leu Asn Asn Gln Val Ile Lys Phe
    210                 215                 220

Arg Gln Asp Asn Asn Leu Xaa
225                 230

<210> SEQ ID NO 34
<211> LENGTH: 10
<212> TYPE: PRT
<213> ORGANISM: Artificial Sequence
<220> FEATURE:
<223> OTHER INFORMATION: Linker

<400> SEQUENCE: 34

Gly Gly Gly Gly Ser Gly Gly Gly Gly Ser
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Linker

<400> SEQUENCE: 35

Gly Gly Gly Gly Ser Gly Gly Gly Gly Ser Gly Gly Gly Gly Ser
1               5                   10                  15

<210> SEQ ID NO 36
<211> LENGTH: 96
<212> TYPE: DNA
<213> ORGANISM: Artificial Sequence -continued

```
<220> FEATURE:
<223> OTHER INFORMATION: E4-TATA

<400> SEQUENCE: 36
tatatatact cgctctgcac ttggcccttt tttacactgt gactgattga gctggtgccg    60
tgtcgagtgg tgtctcgaga tctgcgatct aagtaa                              96

<210> SEQ ID NO 37
<211> LENGTH: 41
<212> TYPE: DNA
<213> ORGANISM: Artificial Sequence
<220> FEATURE:
<223> OTHER INFORMATION: Ad-Late Promoter

<400> SEQUENCE: 37
ggggggctat aaaagggggt ggggggcgttc gtcctcactc t                       41

<210> SEQ ID NO 38
<211> LENGTH: 152
<212> TYPE: DNA
<213> ORGANISM: Artificial Sequence
<220> FEATURE:
<223> OTHER INFORMATION: Tk-minimal promoter

<400> SEQUENCE: 38
gtggccgccc cgactgcatc tgcgtgttca aattcgccaa tgacaagacg ctgggcgggg    60
tttgtgtcat catagaacta aagacatgca aatatattc ttccggggac accgccagca   120
aacgcgagca acgggccacg gggatgaagc ag                                 152
```

LIGAND-REGULABLE TRANSACTIVATION SYSTEMS, METHODS OF USE THEREOF, METHODS OF DETECTING ESTROGEN RECEPTOR LIGANDS, AND METHODS OF DIFFERENTIATING ESTROGEN RECEPTOR LIGAND AGONISTS AND ANTAGONISTS

CROSS-REFERENCE TO RELATED APPLICATION

This application is a divisional application of U.S. Utility Application entitled "LIGAND-REGULABLE TRANSACTIVATION SYSTEMS, METHODS OF USE THEREOF, METHODS OF DETECTING ESTROGEN RECEPTOR LIGANDS, AND METHODS OF DIFFERENTIATING ESTROGEN RECEPTOR LIGAND AGONISTS AND ANTAGONISTS" having Ser. No. 11/890,114, filed Aug. 3, 2007, now issued as U.S. Pat. No. 7,709,253, which claims priority to U.S. provisional application entitled, "LIGAND-REGULABLE TRANSACTIVATION SYSTEMS, METHODS OF USE THEREOF, METHODS OF DETECTING ESTROGEN RECEPTOR LIGANDS, AND METHODS OF DIFFERENTIATING ESTROGEN RECEPTOR LIGAND AGONISTS AND ANTAGONISTS," having Ser. No. 60/835,674, filed on Aug. 4, 2006, which is entirely incorporated herein by reference.

STATEMENT REGARDING FEDERALLY SPONSORED RESEARCH OR DEVELOPMENT

This invention was made with Government support under contracts CA082214 and CA114747 awarded by the National Institutes of Health. The Government has certain rights in this invention.

BACKGROUND

Gene therapies hold the potential application in treating many genetic disorders. The success of gene therapies mainly depends on many different factors; one among them is the availability of regulable gene expression systems. The use of regulable gene expression systems is not only restricted to gene therapy applications; they are also useful for different functional genomic studies and clinical applications in mammals. As gene therapy research continuously progresses, the need for regulable gene expression systems becomes more apparent. An efficient regulable gene expression system should have the quality in controlling the level of expressed transgenes in a dose dependent manner in response to externally administered pharmacological agents. In addition, the regulable gene expression system should also have the ability in producing low level of background signal before administering the activators/regulators.

So far, several regulable gene expression systems have been developed and used for different applications. The very early systems include the naturally occurring physical and chemical stimuli responsive promoters such as heat shock, electric, light and heavy metal inducible promoters. Even though these natural promoters have the potential in controlling the level of transgene expression, adopting them for mammalian gene therapy application is difficult because of hazardous effects associated with the inducers. To overcome these issues, later combination elements derived from prokaryotic and eukaryotic systems were used for developing controlled gene expression systems. These systems are efficient for utilization in mammalian cells in vitro and in vivo. Most of these systems utilize either one or a combination of the following elements that includes DNA binding domains, ligand binding domains and transactivation domains. The systems developed by using these elements include tetracycline regulated system, mifepristone (RU486) regulated system, ecdysone regulated system, rapamycin regulated system, tamoxifen regulated system and ligand activated site specific recombination system (Cre-ER). Even though all these systems showed significant levels of transgene expression in response to externally administered pharmacological agents, many of them produced significant levels of background signal before administering the activators.

Estrogens are responsible for the growth, development and maintenance of many reproductive cells. The physiological effects of these hormones are mediated by a ligand-inducible nuclear transcription factor, the estrogen receptor (ER). In the classical pathway of steroid hormone action, 17β-estradiol binds to the ligand binding domain (LBD) of an estrogen receptor and induces homodimerization, which then binds to a specific regulatory sequence of promoters of ER target genes, the estrogen response elements (ERE). The binding of hormones and a variety of other chemicals to the LBD of ER leads to a series of molecular events. This includes the activation or repression of many downstream target genes through direct interaction with the transcription machinery.

Abnormal levels of estrogen have been linked with many disorders including cancer. The deficiency in the level of estrogen in post menopausal women can lead to reduced bone densities. Similarly, the presence of excess hormones has been reported to induce the development of different types of cancers including breast cancer. Most of these cancers respond to hormonal therapy (anti-estrogens) via the estrogen receptor. Hence, estrogen receptors are a major cellular therapeutic target.

The ER-LBD is folded into a three-layered, anti-parallel, α-helical sandwich composed of a central core layer of three helices that includes H5/6, H9, and H10. This is in turn sandwiched between two additional layers of helices (H1-4 and H7, H8, H11). This helical arrangement creates a "wedge shaped" molecular scaffold that maintains a sizeable ligand binding property at the narrower end of the domain. The remaining secondary structural elements, a small two-stranded, anti-parallel β-sheet (S1 and S2) and an α-helical H12, are located at this ligand binding portion of the molecule and flank the three-layered motif. The helix 12 (H12) is mainly located in the pocket of the ligand binding region. Therefore, it is a key element of the receptor in developing conformational modifications in response to various ligands. The crystal structures of the LBD complexed with 17β-estradiol and Raloxifene show that although both ligands bind at the same site within the core of the LBD, each of these ligands induces a different conformational change on H12. In addition, the binding of ligands to the ligand-binding domain of ERα causes a conformational shift of helix 12 into an adjacent co-activator site that either prevents or enhances ERα from binding to a co-activator (NR box peptide), which would then activate a specific DNA sequence, the estrogen response element (ERE). This process controls many genes that are responsible for cell growth. Hence, helix 12 is one of the major portions of ER that plays a critical role in the ligand induced proliferative effect of cells, and it is therefore important to develop an assay based on the movement of helix 12 in response to different ligands.

SUMMARY

Briefly described, embodiments of this disclosure include ligand-regulable transactivation systems, methods of producing ligand-regulable transactivation systems, methods of using ligand-regulable transactivation systems, reporter polynucleotides, methods of producing reporter polynucleotides, activator fusion proteins, method of producing activator fusion proteins, methods of regulating gene expression in vitro and in vivo for gene therapy, methods of screening estrogen receptor modulators with therapeutic treatments (e.g., anticancer, antiosteoporosis, and hormone replacement treatments), methods of screening compounds (e.g., drugs and environmental pollutants) for the estrogenic effect, methods of evaluating the estrogen receptor pathway under different pathological conditions, and the like.

One exemplary ligand-regulable transactivation system, among others, includes: a reporter polynucleotide that includes a binding sequence, a promoter sequence, and a reporter sequence, wherein the binding sequence is connected with the promoter sequence and the promoter sequence is connected with the reporter sequence; and an activator fusion protein that includes a DNA binding domain, an estrogen receptor folding domain, and a transactivation domain, wherein the DNA binding domain is connected to the estrogen receptor folding domain, and the estrogen receptor folding domain is connected with the transactivation domain.

In an embodiment, the ER folding domain has a characteristic of changing from a first conformational position to an interacting conformational position or an non-interacting conformational position upon interaction with a compound; wherein the interacting conformational position positions the DNA binding domain and the transactivation domain so that both interact with the binding sequence and the promoter sequence of the reporter polynucleotide, which causes the reporter sequence to generate a bioluminescent protein that is detectable; wherein the non-interacting conformational position does not position the DNA binding domain and the transactivation domain so that both interact with the binding sequence and the promoter sequence of the reporter polynucleotide.

In an embodiment, the interacting conformation position corresponds to one of two states including substantially interacting and partially interacting, wherein substantially interacting means that the DNA binding domain and the transactivation domain interact with the binding sequence and the promoter sequence of the reporter polynucleotide to a greater degree than partially interacting and non-interacting, and wherein partially interacting means that the DNA binding domain and the transactivation domain interact with the binding sequence and the promoter sequence of the reporter polynucleotide to a greater degree than non-interacting.

One exemplary method of detecting a ligand, among others, includes: providing an ligand-regulable transactivation system of described herein; introducing a ligand to the system; and detecting a bioluminescent signal in the presence of a bioluminescence initiating compound if the ligand causes the ER folding domain to change from a first conformational position to an interacting conformational position.

One exemplary cell, among others, includes: a ligand-regulable transactivation system having: a reporter polynucleotide that includes a binding sequence, a promoter sequence, and a reporter sequence, wherein the binding sequence is connected with the promoter sequence and the promoter sequence is connected with the reporter sequence; and an activator fusion protein that includes a DNA binding domain, an estrogen receptor folding domain, and a transactivation domain, wherein the DNA binding domain is connected to the estrogen receptor folding domain, and the estrogen receptor folding domain is connected with the transactivation domain.

One exemplary transgenic animal, among others, includes: a ligand-regulable transactivation system having: a reporter polynucleotide that includes a binding sequence, a promoter sequence, and a reporter sequence, wherein the binding sequence is connected with the promoter sequence and the promoter sequence is connected with the reporter sequence; and an activator fusion protein that includes a DNA binding domain, an estrogen receptor folding domain, and a transactivation domain, wherein the DNA binding domain is connected to the estrogen receptor folding domain, and the estrogen receptor folding domain is connected with the transactivation domain.

One exemplary fusion protein, among others, includes: a ligand-regulable transactivation system having: a reporter polynucleotide that includes a binding sequence, a promoter sequence, and a reporter sequence, wherein the binding sequence is connected with the promoter sequence and the promoter sequence is connected with the reporter sequence; and an activator fusion protein that includes a DNA binding domain, an estrogen receptor folding domain, and a transactivation domain, wherein the DNA binding domain is connected to the estrogen receptor folding domain, and the estrogen receptor folding domain is connected with the transactivation domain.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Co-transfecting with 10 ng of plasmid expressing *Renilla* luciferase normalized the transfections. The SEM of triplicate reading was used.

Figure 4:
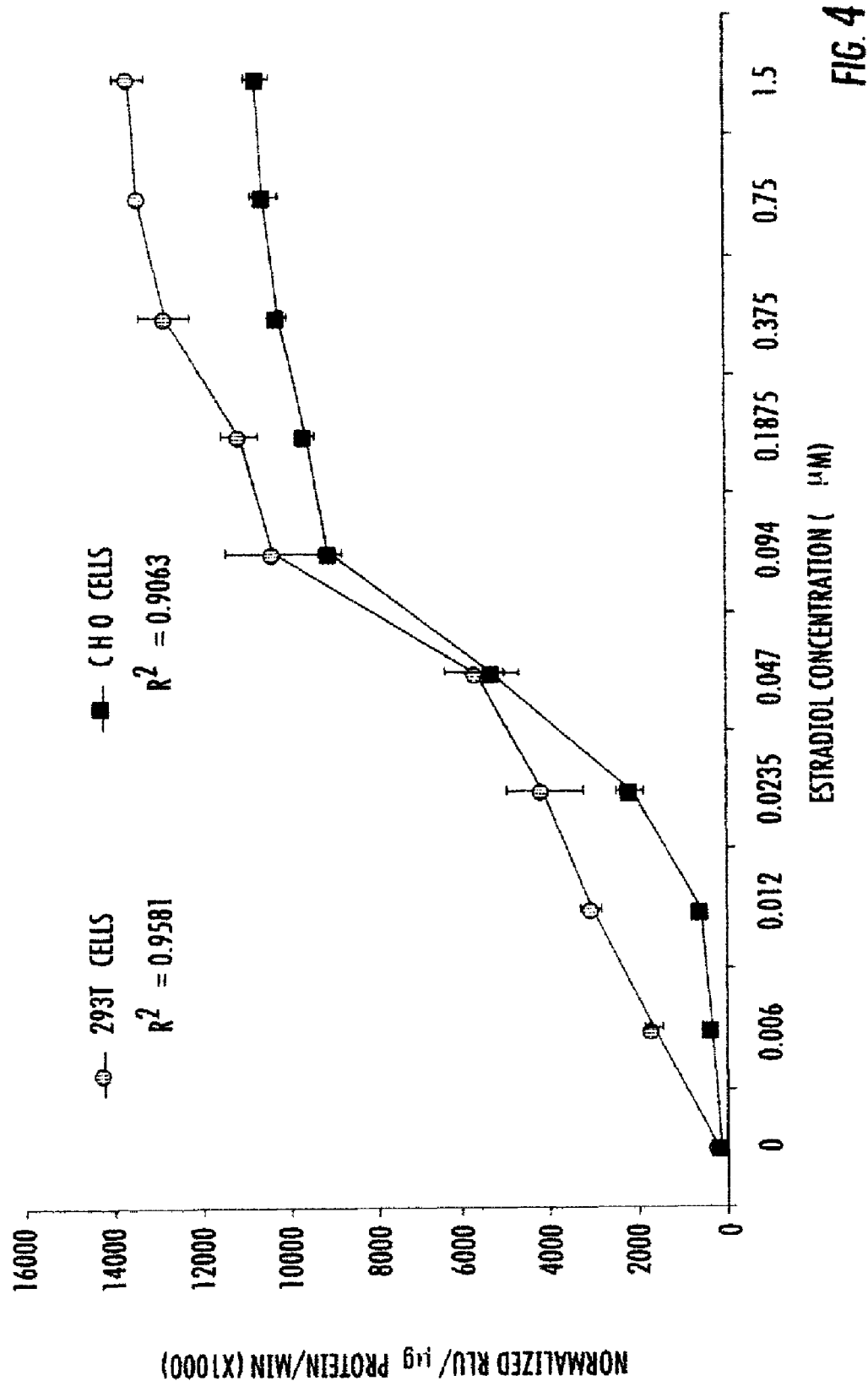

FIG. 4 illustrates a graph of the concentration dependent transactivation of reporter gene expression by the system. Ligand concentration dependent transactivation of reporter gene expression was studied in 293T and CHO cells co-transfected with the reporter plasmid and the activator plasmid expressing GAL4-ER (LBD)-VP16 fusion protein. The cells were assayed for luciferase activity after exposed to 10 different concentrations of ligand 17β-estradiol. The results were normalized by co-transfecting 10 ng of *Renilla* luciferase plasmid. The error bars are the SEM of triplicate determinations.

FIG. 5A is a graph that illustrates the system's utility in controlling with different ER-ligands. The 293T cells co-transfected with the reporter plasmid and the activator plasmid expressing fusion protein GAL4-ER (LBD)-VP16 were induced with different ER-ligands, inducing agonists, antagonists, partial agonists and partial antagonists. As negative control, a non-ER binding anticancer drug cisplatinum was used. The results were normalized by co-transfecting 10 ng of *Renilla* luciferase plasmid. The error bars are the SEM of triplicate determinations.

FIG. 5B is a Western blot analysis of the corresponding samples that were analyzed with ER-antibody and Firefly luciferase antibody to confirm the ligand-induced transactivation of the system.

Figure 6A:
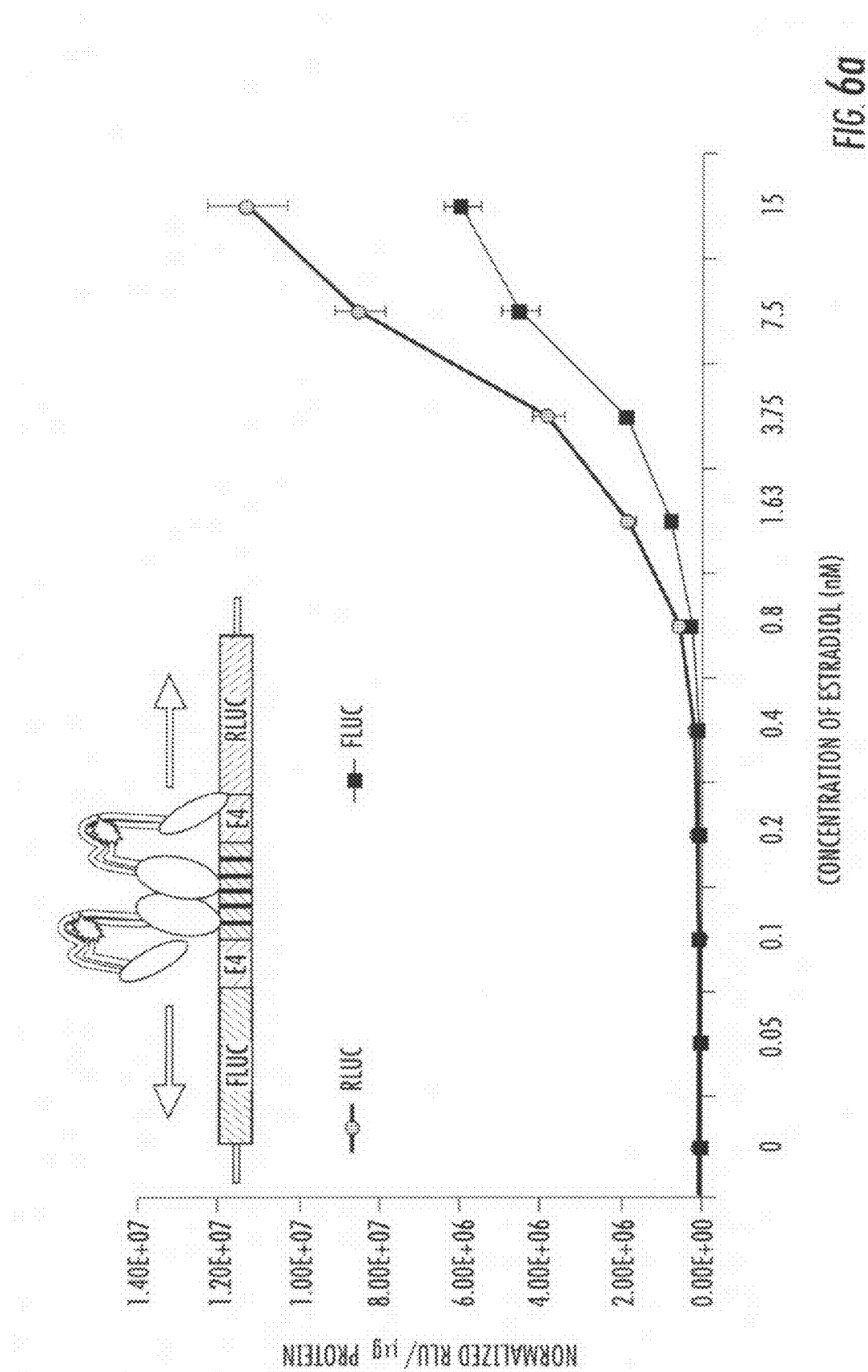

FIG. 6A is a graph that illustrates the efficiency of ER ligand mediated transactivation system in controlling two different genes expressing from a single bi-directional vector in two different orientations studied by exposing the transiently co-transfected cells with reporter and the plasmid expressing GAL4-ER-VP16 fusion protein with 12 different concentrations of ligand 17β-estradiol.

Figure 6B:
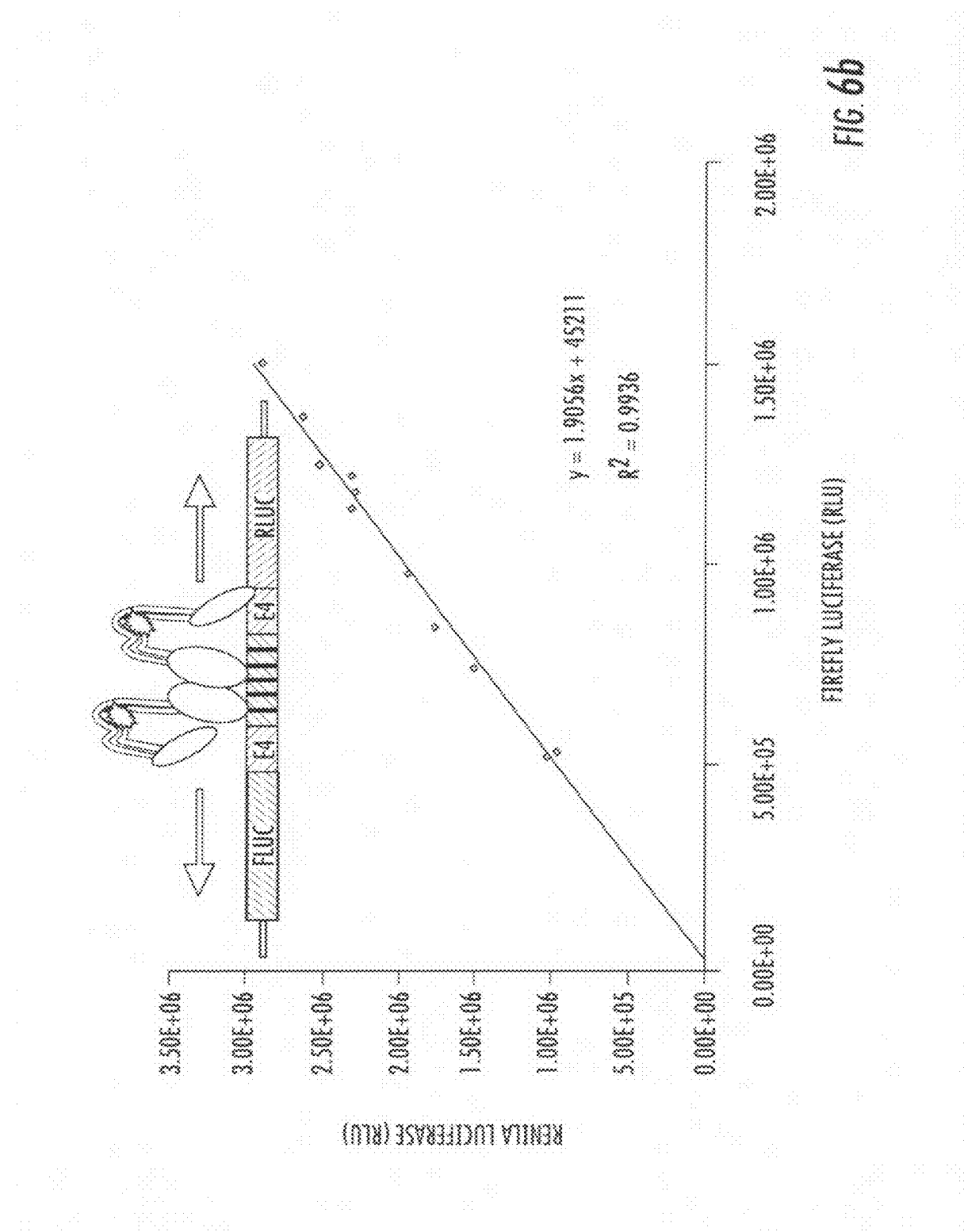

FIG. 6B is a graph that illustrates that the results showed significant correlation ($R^2=0.9936$) with concentration of ligand and the expression level of two reporter proteins *Renilla* and firefly luciferases. The error bars are the SEM of triplicate determinations.

Figure 7:
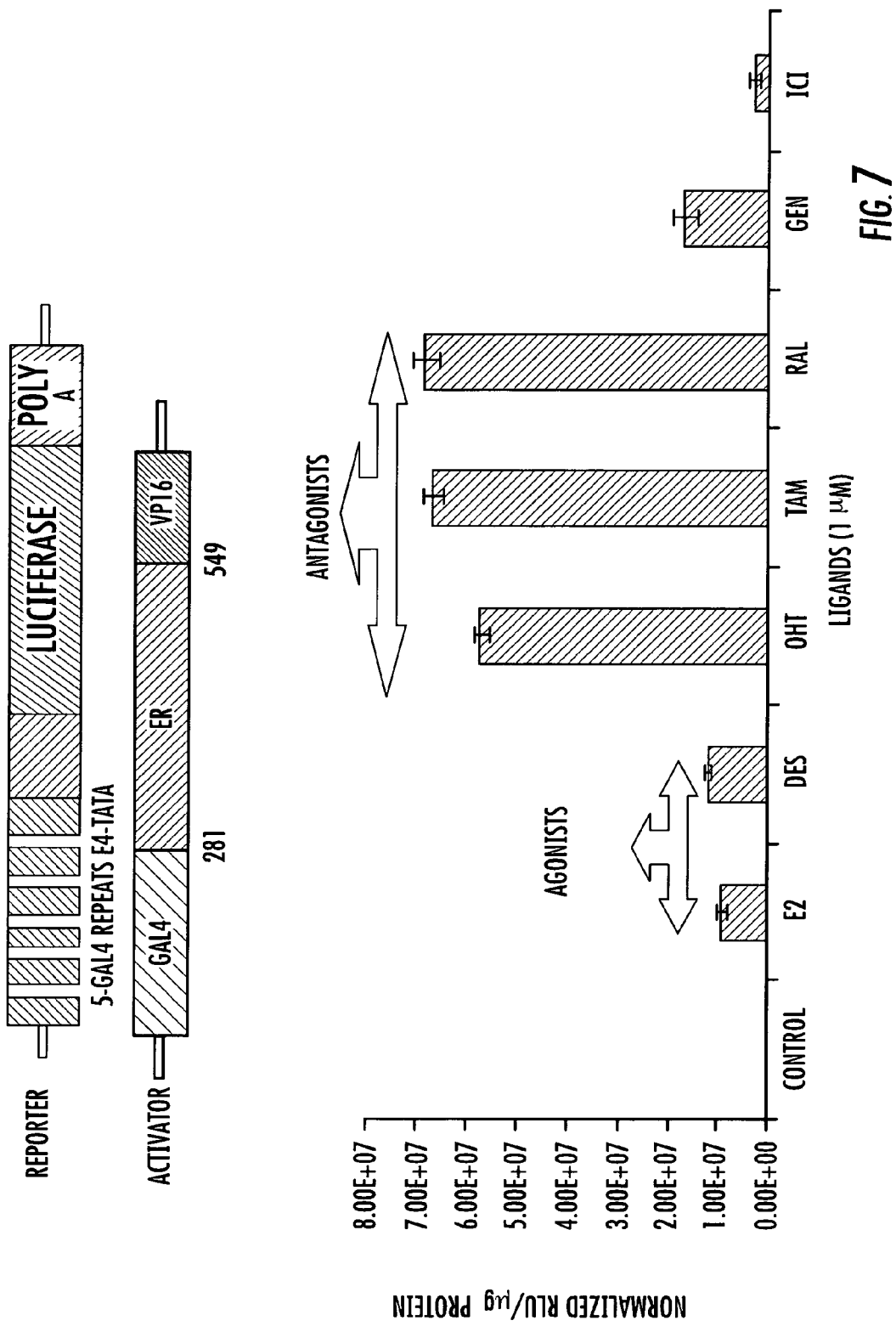

FIG. 7 is a graph illustrating the application of a ligand induced transactivation system developed for differentiating ER-ligands. The 293T cells co-transfected with the reporter plasmid and the activator plasmid expressing ER-ligand binding domain of amino acids 281-549 were used for differentiating ER-ligands. The cells were assayed for luciferase activity after exposure to 1 μM concentration of different ligands. The system showed ligand dependent activation for different ligands used for the study. The results were normalized by co-transfecting with 10 ng of *Renilla* luciferase plasmid. The error bars are the SEM of triplicate determinations.

Figure 8:
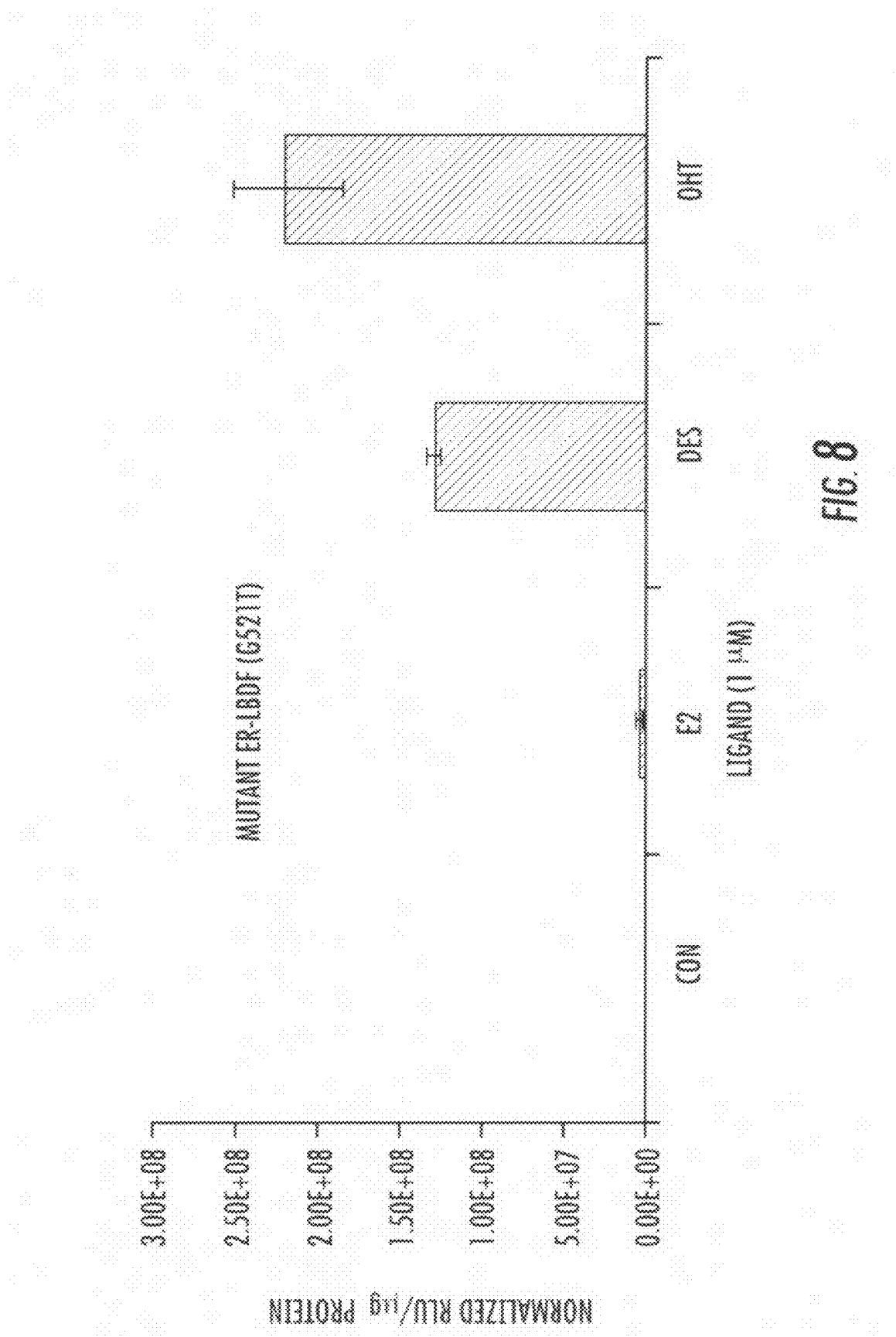

FIG. 8 is a graph illustrating the application of ligand induced transactivation system developed with the mutant form of ER-LBD. To extend the systems utility in living animals we developed ER-ligand regulated transactivation system with a mutant form of ER-LBD (G521T) identified from our previous study that specifically had very low affinity for the endogenous estrogen 17-β estradiol. The 293T cells co-transfected with reporter and the activator plasmid expressing GAL4-ER-VP16 with mutant form of estrogen receptor showed low affinity specifically for estradiol only with the transactivation system also. The results were normalized by co-transfecting with 10 ng of *Renilla* luciferase plasmid. The error bars are the SEM of triplicate determinations.

FIG. 9A illustrates images to show the efficiency of ER ligand regulated transactivation system in controlling the reporter gene expressions studied in living animals by non-invasive optical CCD camera imaging. To study that, the nude mice of six weeks old (5 each for ligand induced and solvent control) were implanted with 5 million 293T cells transiently co-transfected with reporter plasmid and the plasmid expressing GAL4-ER-VP16. They were imaged immediately and once every 24 hours before and after inducing with ER ligand antagonist Raloxifene (20 mg/kg body weight). The result showed significant levels of reporter gene expression only from the animals that received ligand Raloxifene.

FIG. 9B illustrates the quantitative analysis of the results from different time points studied. The error bars are the SEM of triplicate determinations.

DETAILED DESCRIPTION

Embodiments of the present disclosure will employ, unless otherwise indicated, techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

In describing and claiming the disclosed subject matter, the following terminology will be used in accordance with the definitions set forth below.

A "bioluminescent initiator molecule" is a molecule that can react with a bioluminescent protein to generate bioluminescence.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall (homologous) and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biologically functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also refers to the degree of sequence relatedness between polypeptides as determined by the match between strings of such sequences. "Identity" and "similarity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073, (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present invention.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution (including conservative and non-conservative substitution), or insertion, and wherein said alterations may occur at the amino- or carboxy-terminus positions of the reference polypeptide sequence or anywhere between those terminal positions, interspersed either individually among the amino acids in the reference sequence, or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. (Robertson, et al., *J. Am. Chem. Soc.*, 113: 2722, 1991; Ellman, et al., *Methods Enzymol.*, 202: 301, 1991; Chung, et al., *Science*, 259: 806-9, 1993; and Chung, et al., *Proc. Natl. Acad. Sci. USA*, 90: 10145-9, 1993). In a second method, translation is carried out in *Xenopus* oocytes by microinjection of mutated mRNA and chemically aminoacylated suppressor tRNAs (Turcatti, et al., *J. Biol. Chem.*, 271: 19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., *Biochem.*, 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., *Protein Sci.*, 2: 395-403, 1993).

As used herein, the term "polynucleotide" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompass a polynucleotide as defined above.

In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including simple and complex cells, inter alia.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminus positions of the reference nucleotide sequence or anywhere between those terminus positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

The term "codon" means a specific triplet of mononucleotides in the DNA chain or mRNA that make up an amino acid or termination signal.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins, or the nucleic acid may be incorporated into a vector.

As used herein, the term "vector" or "expression vector" is used to denote a DNA molecule, linear or circular, which includes a segment encoding a polypeptide of interest operably linked to additional segments that provide for its transcription and translation upon introduction into a host cell or host cell organelles. Such additional segments include promoter and terminator sequences, and may also include one or more origins of replication, one or more selectable markers, an enhancer, a polyadenylation signal, etc. Expression vectors are generally derived from yeast or bacterial genome or plasmid DNA, animal virus genome, or viral DNA, or may contain elements of both.

"DNA regulatory sequences", as used herein, are transcriptional and translational control sequences, such as promoters, enhancers, polyadenylation signals, termination signals, and the like, that provide for and/or regulate expression of a coding sequence in a host cell.

A "promoter sequence" is a DNA regulatory region in an operon capable of binding RNA polymerase in a cell and initiating transcription of a downstream (3' direction) coding sequence. For purposes of defining the present invention, the promoter sequence is bound at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

The terms "chimeric", "fusion" and "composite" are used to denote a protein, peptide domain or nucleotide sequence or molecule containing at least two component portions that are mutually heterologous in the sense that they are not, otherwise, found directly (covalently) linked in nature. More specifically, the component portions are not found in the same continuous polypeptide or gene in nature, at least not in the same order or orientation or with the same spacing present in the chimeric protein or composite domain. Such materials contain components derived from at least two different proteins or genes or from at least two non-adjacent portions of the same protein or gene. Composite proteins, and DNA sequences that encode them, are recombinant in the sense that they contain at least two constituent portions that are not otherwise found directly linked (covalently) together in nature.

The term "domain" in this context is not intended to be limited to a single discrete folding domain.

A "reporter polynucleotide" includes any gene that expresses a detectable gene product, which may be RNA or a reporter polypeptide. Reporter genes include coding sequences for which the transcriptional and/or translational product are readily detectable or selectable.

As used herein, the term "hybridization" refers to the process of association of two nucleic acid strands to form an antiparallel duplex stabilized by means of hydrogen bonding between residues of the opposite nucleic acid strands.

"Hybridizing" and "binding", with respect to polynucleotides, are used interchangeably. The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the disclosure can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions sets forth the conditions that determine whether a nucleic acid will specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, substantially similar conditions. Stringent conditions for washing can also be, e.g., 0.2×SSC/0.1% SDS at 42° C.

A specific example of stringent assay conditions is a rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature.

Stringent assay conditions are hybridization conditions that are at least as stringent as the above representative conditions, where a given set of conditions are considered to be "at least as stringent" if substantially no additional binding complexes that lack sufficient complementarity to provide for the desired specificity are produced in the given set of conditions as compared to the above specific conditions, where by "substantially no more" is meant less than about 5-fold more, typically less than about 3-fold more.

By "administration" is meant introducing a sensor of the present disclosure into a subject. The preferred route of administration of the sensor is intravenous. However, any route of administration, such as oral, topical, subcutaneous, peritoneal, intraarterial, inhalation, vaginal, rectal, nasal, introduction into the cerebrospinal fluid, or instillation into body compartments can be used.

In accordance with the present disclosure, "a detectably effective amount" of the sensor of the present disclosure is defined as an amount sufficient to yield an acceptable image using equipment that is available for clinical use. A detectably effective amount of the sensor of the present disclosure may be administered in more than one injection. The detectably effective amount of the sensor of the present disclosure can vary according to factors such as the degree of susceptibility of the individual, the age, sex, and weight of the individual, idiosyncratic responses of the individual, the dosimetry, and the like. Detectably effective amounts of the sensor of the present disclosure can also vary according to instrument and film-related factors. Optimization of such factors is well within the level of skill in the art.

As used herein the term "isolated" is meant to describe a polynucleotide, a polypeptide, an antibody, or a host cell that is in an environment different from that in which the polynucleotide, the polypeptide, the antibody, or the host cell naturally occurs.

As used herein, the term "organelle" refers to cellular membrane-bound structures such as the chloroplast, mitochondrion, and nucleus. The term "organelle" includes natural and synthetic organelles.

As used herein, the term "non-nuclear organelle" refers to any cellular membrane bound structure present in a cell, except the nucleus.

As used herein, the term "host" or "organism" includes humans, mammals (e.g., cats, dogs, horses, etc.), living cells, and other living organisms. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications.

General Discussion

Embodiments of the present disclosure include: ligand-regulable transactivation systems, methods of producing ligand-regulable transactivation systems, methods of using ligand-regulable transactivation systems, reporter polynucleotides, methods of producing reporter polynucleotides, activator fusion proteins, methods of producing activator fusion proteins, methods of regulating gene expression in vitro and in vivo for gene therapy, methods of screening estrogen receptor modulators with therapeutic treatments (e.g., anti-cancer, antiosteoporosis, and hormone replacement treatments), methods of screening compounds (e.g., drugs and environmental pollutants) for the estrogenic effect, and methods of evaluating the estrogen receptor pathway under different pathological conditions.

The ligand-regulable transactivation system includes a reporter polynucleotide and an activator fusion protein. The reporter polynucleotide includes, but is not limited to, a binding sequence, a promoter sequence, and a reporter sequence. The binding sequence is connected (e.g., directly or indirectly with a linker) with the promoter sequence, and the promoter sequence is connected (e.g., directly or indirectly with a linker) with the reporter sequence. The activator fusion protein includes, but is not limited to, a DNA binding domain, an estrogen receptor folding domain, and a transactivation domain. The DNA binding domain is connected (e.g., directly or indirectly with a linker) to the estrogen receptor folding domain, and the estrogen receptor folding domain is connected (e.g., directly or indirectly with a linker) with the transactivation domain. An illustrative embodiment of the ligand-regulable transactivation system is discussed in reference to Example 1 and depicted in FIG. 1.

Embodiments of the present disclosure can be used in cell cultures and in living animals by customizing the reporter sequence (polynucleotide), while not changing the activator fusion protein. In an embodiment, if the aim of the study is for a therapeutic approach for cancer therapy it is possible to introduce thymidine kinase (suicidal therapeutic gene) in the place of luciferase. In another embodiment, if the aim is to correct some naturally defective gene, it is possible to introduce that particular gene in active form in the place of luciferase.

Embodiments of the present disclosure can be used to screen a library of compounds for their estrogen receptor (ER) binding properties. In addition, embodiments of the present disclosure can be designed to distinguish between ER ligands and non-ER ligands and between/among ER agonists, partial ER agonists, ER antagonists, partial ER antagonists, and/or Selective Estrogen Receptor Modulators (SERMs) by exposing the compound to a cell line or host transfected with the reporter polynucleotide and the activator fusion protein vector or with a transgenic animal incorporating the ligand-regulable transactivation system.

Illustrative embodiments of the agonists can include, but are not limited to, estradiol, diethylstilbestrol, diarylpropionitrile, genistein and tetrahydrocannabinol. Illustrative embodiments of the antagonists can include, but are not limited to, methylpiperidinopyrazole and ICI 182780. Illustrative embodiments of the SERM can include, but are not limited to, hydroxytamoxifen, raloxifene, and tamoxifen. It should be noted that SERMs tend to have a mixed action (agonist and antagonist), but tend to be more similar to how an antagonist affects embodiments of the present disclosure. Distinguishing a SERM from an agonist and/or an antagonist can be conducted in a similar manner as described below for an agonist and an antagonist.

As mentioned above, the activator fusion protein includes the DNA binding domain, the ER folding domain, and the transactivation domain. The ER folding domain can be designed in such a way that it can distinguish between different types of compounds and be used in different systems. For example, the ER folding domain can be designed to distinguish between ER ligands and non-ER ligands and between/among ER agonists, partial ER agonists, ER antagonists, partial ER antagonists, and/or SERMs. In another example, the ER folding domain can be designed to reduce interaction between the ER ligand binding domain and endogenous ER ligands (e.g., 17β-estradiol). Reducing the interaction with the endogenous ER ligands enhances the ligand-regulable transactivation system's ability to be used in living hosts.

In an embodiment, the ER folding domain has a folding arrangement in a three-dimensional space. The ER folding domain can undergo a conformation change into one or more folding arrangements under the inducement of a compound (e.g., ER ligands, and ER agonists, partial ER agonists, ER antagonists, partial ER antagonists, and SERMs).

In an embodiment, the interaction of the ER folding domain with a first compound (or first type or class of compound) (e.g., antagonist, See Example 1) alters the activator fusion protein to a first conformational position (e.g., a three-dimensional folding arrangement). In the first conformational position, the transactivation domain of the fusion protein bound with the binding sequence can substantially interact with the promoter sequence and activates the promoter to transcribe the reporter polynucleotide, which causes the reporter sequence to generate a bioluminescent protein (or in another embodiment a fluorescent protein or enzyme). The bioluminescent protein can interact with a first amount of a bioluminescence initiating compound (or compound appropriate for the fluorescent protein or enzyme) to produce an emission that can be detected and measured. Thus, embodiments of the present disclosure can be used to detect, measure, quantitate, image, and the like, interactions of compounds with the ER folding domain of the activator fusion protein.

In an embodiment, the interaction of the ER folding domain with a second compound (or second type or class of compound) (e.g., agonist, See Example 1) alters the activator fusion protein to a second conformational position. The second conformational position positions the DNA binding domain and the transactivation domain so that both can interact with the binding sequence and partially activate the promoter sequence of the reporter polynucleotide, which causes the reporter sequence to generate a second amount of a bioluminescent protein. The bioluminescent protein can interact with a bioluminescence initiating compound to produce an emission that can be detected and measured. Thus, embodiments of the present disclosure can be used to detect, measure, quantitate, image, and the like, interactions of compounds with the ER folding domain of the activator fusion protein.

In an embodiment, the interaction of the ER folding domain with a third compound (or third type or class of compound) (e.g., control, See Example 1) alters the activator fusion protein to a third conformational position. The third conformational position positions the DNA binding domain and the transactivation domain so that both do not interact with the binding sequence and activate to a negligible degree (less than about 1% of the first confirmation) of the promoter sequence of the reporter polynucleotide, and the reporter sequence does not generate a bioluminescent protein. Thus, embodiments of the present disclosure can be used to detect, measure, quantitate, image, and the like, interactions of compounds with the ER folding domain of the activator fusion protein.

The first amount of bioluminescent protein is greater than the second amount of bioluminescent protein. Thus, the amount of bioluminescent energy generated by the first compound (e.g., antagonist) is greater than and distinguishable from the amount of bioluminescent energy generated by the second compound (e.g., agonist). It should be noted that a plurality of second compounds could be distinguished among one another based on relatively different amounts of partial interaction. Therefore, an antagonist, partial antagonist, an agonist, and a partial agonist are distinguishable using embodiments of the present disclosure.

The term "substantially interact" means that the first conformational position of the DNA binding domain and the transactivation domain interact with the binding sequence and the promoter sequence of the reporter polynucleotide to a greater degree than when the ER folding domain is in the second conformational position.

The term "partially interact" means that the second conformational position of the DNA binding domain and the transactivation domain interact with the binding sequence and the promoter sequence of the reporter polynucleotide to a greater degree than when the ER folding domain is in the third conformational position. As mentioned above, the term "partially interact" can correspond to a plurality of second conformational positions, and each partial interaction could be distinguishable from other partial interactions.

In other words, there can be a measurable and statistically significant difference (e.g., a statistically significant difference is enough of a difference to distinguish among the different states, such as about 0.1%, 1%, 3%, 5%, 10%, 15%, 20%, 25%, 30%, or 40% or more difference between the amount of energy emitted in each state, where the statistically significant difference is determined, at least in part, by the components of the ligand-regulable transactivation system as well as the detection system) between "substantially interact" and "partially interact", between "partially interact" and "does not interact", and between two degrees of "partially interact" for two different ligands that partially interact with the ER folding domain. The measurable difference can be used to distinguish between instances where a particular ligand substantially interacts, partially interact(s), or does not interact. Standards can be used to determine the relative amount of energy that is emitted. Additional details are described in the Example.

Embodiments of the present disclosure can be used to detect, study, monitor, evaluate, and/or screen, biological events in vivo and/or in vitro, such as, but not limited to, ER related interactions with ER ligands and non-ER-ligands. In addition, embodiments of the present disclosure can be used to screen molecules (e.g., drugs) related to the ER interactions with ER ligands and non-ER-ligands using methods described herein are methods similar to those described herein.

Embodiments of the present disclosure can be used to detect (and visualize) and/or quantitate ER related interactions events in in vitro as well as in in vivo studies, which can decrease time and expense since the same system can be used for cells and living organisms. Embodiments of the present disclosure can be used to test an event occurrence in a large number of samples, and has the capacity to transition from single cells to living animals without changing or substantially changing the ligand-regulable transactivation system. In an embodiment, the ER folding domain is the only portion of the ligand-regulable transactivation system that is changed.

In an embodiment, the ligand-regulable transactivation system can be used in methods of detecting an ER agonist and an ER antagonist using a ligand-regulable transactivation system having a ER folding domain designed to distinguish between ER agonists and ER antagonists (See Example 1). The ligand-regulable transactivation system or components thereof are expressed in, introduced to, and/or are part of a cell or a host. A ligand is introduced to the cell or host. The ER ligand (e.g., agonist, antagonist, or SERMs) may interact with the ER folding domain and may cause a conformational change as described above. Upon interaction of the activator fusion protein with the reporter polynucleotide, a bioluminescent protein is generated. A bioluminescence initiating compound is introduced to the system (prior to and/or after the agonist or antagonist). If a bioluminescent signal is detected, a conformational change occurred. If no bioluminescent signal is detected, a conformational change did not occur. The intensity and/or strength of the bioluminescent signal can be used to determine if the ligand is an agonist (or partial agonist), antagonist (or partial antagonist), or SERM.

Standards could be used to assist in determining the relative strength between energy admitted as a result of an agonist and an antagonist. Additional details are described in the Example.

It should be noted that the same or similar methods and the same or similar ligand-regulable transactivation systems (e.g., one could modify the ER folding domain in accordance with the compounds and/or conditions being tested) could be used for distinguishing among ER agonists, partial ER agonists, ER antagonists, partial ER antagonists, and/or SERMs by changing the length of ER-ligand binding domain of amino acids 281-549 instead of 281-595 in the activator fusion protein.

In addition, the same or similar methods and the same or similar ligand-regulable transactivation systems can be used in methods of screening estrogen receptor modulators with therapeutic treatments (e.g., anticancer, antiosteoporosis, and hormone replacement therapies).

Further, the same or similar methods and the same or similar ligand-regulable transactivation systems can be used in methods of screening compounds (e.g., drugs and environmental pollutants) for the estrogenic effect.

Furthermore, the same or similar methods and the same or similar ligand-regulable transactivation systems can be used in methods of evaluating the estrogen receptor pathway under different pathological conditions by using the activator fusion protein containing the ER-ligand binding domain of both the lengths (amino acids 281-549 and 281-595).

Note that for each ligand-regulable transactivation system, protein, fusion protein, protein fragment, and nucleotide, one skilled in the art would be able to determine the corresponding nucleotide sequence or protein sequence, respectively, and be able to introduce or express each into a system of interest.

In general, ligand-regulable transactivation system can be used in vivo and/or in vitro. In an embodiment, the ligand-regulable transactivation system or components thereof can be introduced into a system (e.g., inside a cell or outside a cell and/or a to host), the ligand-regulable transactivation system or components thereof can be expressed (e.g., using a vector) in the system, and/or the ligand-regulable transactivation system or components thereof can be included in a transgenic animal or plant. In an embodiment, the ligand-regulable transactivation system or components thereof can be introduced into a host or organism in vivo.

The methods of the present disclosure can be conducted in vitro or in vivo. The ligand-regulable transactivation system or components thereof can be introduced, incorporated into, or expressed in a part of a cell or a host. The host can include a transgenic animal or transgenic plant.

In another embodiment, the ER folding domain can be designed to reduce interaction between the ER folding domain and endogenous ER ligands. This mutation enhances the ability to use the ER intramolecular folding system in living hosts. In this regard, the ER folding domain is designed to reduce the interaction between the ER folding domain and 17β-estradiol. In an embodiment, the sequence of the ER folding domain can be modified by changing the amino acid at a position 521 from glycine to threonine (SEQ. ID No. 3), which reduced interaction of the ER folding domain with 17β-estradiol by about 95%, while only reducing the interaction of the ER folding domain with other ER ligands by about 10-20%. The change from glycine to threonine (SEQ. ID Nos. 3, 23, and 24) was conducted by creating a mutation at 521 with all 20 amino acids and screening with more than 10 ER-ligands. It should also be noted that in other embodiments the amino acid at position 521 could be changed from glycine to any one of the other amino acids (e.g., the other 19 amino acids (e.g., SEQ ID Nos. 23, 24, 25, and 26), which is described in more detail in the Example.

Activator Fusion Protein

As mentioned above, the activator fusion protein includes, but is not limited to, a DNA binding domain, an estrogen receptor folding domain, and a transactivation domain. Linking polypeptides (described below) can be included in the activator fusion protein to connect one or more of the DNA binding domain, the estrogen receptor folding domain, and the transactivation domain. The activator polynucleotide can encode the activator fusion protein. The activator polynucleotide sequence can be included in an expression system (e.g., a vector) and expressed in a cell line or in a host organism (e.g., prokaryotes or eukaryotes) to produce the activator fusion protein. Methods of producing vectors, other expression systems, (e.g., viral and non-viral) and polynucleotides are well known in the art. It should be noted that the activator fusion protein can be expressed using other expression systems and the vector is merely an illustrative embodiment. Additional details regarding the reporter polynucleotide are discussed in Example 1.

DNA Binding Domain

As used herein, the term "DNA-binding domain" encompasses a small (about 150 amino acids) peptide sequence of a DNA-binding protein, up to the entire length of a DNA-binding protein, so long as the DNA-binding domain functions to associate with a particular response element (e.g., has a specific DNA binding activity towards a DNA sequence). The DNA binding domain refers to the portion of the fusion protein that interacts with the corresponding binding sequence on the reporter polynucleotide. The DNA binding domain can be from Yeast or from another organism that can include, but is not limited to, a bacteria, a human, a mouse, a rat, and the like. The DNA binding domain can include, but is not limited to, GAL4 DNA binding domain (e.g., the transcription factor of yeast) (SEQ. ID. No: 13 (polynucleotide) and 14 (polypeptide)), and the like. The DNA binding domain of the yeast GAL4 protein includes at least the first 74 amino terminal amino acids thereof (SEQ. ID. No: 14) or the GAL4 protein described in the example below (see, for example, Keegan et al., Science 231:699 704 (1986) which is incorporated herein by reference). Preferably, the first 90 or more amino terminal amino acids of the GAL4 protein (SEQ. ID. No: 14) will be used, with the 147 amino terminal amino acid residues of yeast GAL4 (SEQ. ID. No: 14) being presently most preferred.

The DNA binding domain and the binding sequence on the reporter polynucleotide are selected so that they interact in an appropriate manner for the ligand-regulable transactivation system. The selection depends, in part, on one or more of the following: the DNA binding domain, the binding sequence, the ER folding domain, the transactivation domain, the promoter sequence, and the reporter sequence.

Estrogen Receptor Folding Domain

The ER folding domain has already been discussed in detail elsewhere in this disclosure. The ER folding domain can have a sequence selected from: SEQ. ID No. 1 (human estrogen receptor, alpha, amino acids 281-549), SEQ. ID No. 2 (human estrogen receptor, alpha, amino acids 281-595), SEQ. ID No. 3 (human estrogen receptor, alpha, amino acids 1-595), SEQ. ID No. 4 (mouse estrogen receptor, alpha, amino acids 281-549), SEQ. ID No.5 (mouse estrogen receptor, alpha, amino acids 281-599), SEQ. ID No. 6 (mouse estrogen receptor amino acids 1-599) and SEQ. ID No. 27 (estrogen receptor beta).

In an embodiment, the ER folding domain is designed to reduce the interaction between the ER folding domain and 17β-estradiol. In an embodiment, the sequence of the ER folding domain can be modified by changing the amino acid at position 521 from glycine to threonine (SEQ ID Nos. 3, 23 and 24), which reduced interaction of the ER folding domain with 17β-estradiol by about 95%, while only reducing the interaction of the ER folding domain with other ER ligands slightly. Additional details are described in the Example. It should also be noted that the amino acid at position 521 could be changed from glycine to any one of the other amino acids (e.g., the other 19 amino acids (e.g., SEQ ID Nos. 23, 24, 25, and 26)).

Transactivation Domain

A transactivation domain refers to a polypeptide, which acts to activate transcription of a target nucleotide (e.g., gene). The transactivation domain refers to the portion of the fusion protein that interacts with the corresponding promoter sequence on the reporter polynucleotide. The transactivation domain can include, but is not limited to, VP16 transactivation domain (SEQ. ID No: 15 (polynucleotide) and 16 (polypeptide)) and the like.

The transactivation domain and the promoter sequence on the reporter polynucleotide are selected so that they interact in an appropriate manner for the ligand-regulable transactivation system. The selection depends, in part, on one or more of the following: the DNA binding domain, the binding sequence, the ER folding domain, the transactivation domain, the promoter sequence, and the reporter sequence.

Reporter Polynucleotide

In general, a "reporter polynucleotide" includes a polynucleotide that expresses a reporter polypeptide. Reporter polynucleotides include coding sequences for which the transcriptional and/or translational product are readily detectable or selectable (e.g., a bioluminescent protein). As mentioned above, the reporter polynucleotide includes, but is not limited to, a binding sequence, a promoter sequence, and a reporter sequence. The reporter polynucleotide can be included in an expression system (e.g., a vector) and expressed in a cell line or in a host. Methods of producing vectors, other expression systems, (e.g., viral and non-viral) and polynucleotides are well known in the art. It should be noted that the reporter polynucleotide can be incorporated in other expression systems and the vector is merely an illustrative embodiment. Additional details regarding the reporter polynucleotide are discussed in Example 1.

Binding Sequence

A binding sequence is a segment of DNA that is necessary and sufficient to specifically interact with a given polypeptide (e.g., the DNA binding domain). The binding sequence may include the repetition of the same polynucleotide sequence to enhance the activation of downstream protein expression by attracting more DNA binding domains (e.g., provide more than one location for binding). Each of these DNA binding domains can provide more strength for the transcription machinery. The binding sequence can include, but is not limited to, a GAL4 binding sequence (SEQ. ID No: 17) and the like. In an embodiment, since the GAL4 DNA binding domain is from Yeast, a eukaryotic organism, it will have more suitable conditions folding and binding efficiencies when used in these systems in activating genes for gene therapy applications in animals and animal cells.

Promoter Sequence

The promoter sequence is a sequence that enables the reporter polynucleotide to transcribe and generate the bioluminescent protein through processes known in the art such as providing the space for the RNA polymerase to bind and initiate mRNA synthesis. The promoter sequence can include, but is not limited to, an E4 promoter (SEQ. ID No: 36), an E4 minimal promoter (SEQ. ID No: 18), minimal promoter thymidine kinase (tk-promoter) (SEQ. ID No: 37), adenoviral late promoter (SEQ. ID No: 38), and the like. The E4 minimal report may generate a low leaky signal before the system is getting transactivated by transactivation domain.

Reporter Polynucleotides and Polypeptides

The reporter polynucleotide encodes a bioluminescent protein, fluorescent protein, or enzyme that has a detectable substrate either through calorimetric or by other mode that can be quantified. In an embodiment of the present disclosure, the reporter polypeptide can include, but is not limited to, Luciferases or photoproteins. In an embodiment, the reporter polypeptide can include, but is not limited to, *Renilla* Luciferase (the nucleotide sequence is SEQ ID: 7) and the amino acid sequence is SEQ ID: No 8), portions thereof, mutants thereof, variants thereof; Coleoptera Luciferase (the nucleotide sequence is SEQ ID: No 9, and the amino acid sequence is SEQ ID: No 10), portions thereof, mutants thereof, variants thereof; Firefly Luciferase (the nucleotide sequence is SEQ ID: No 11 and the amino acid sequence is SEQ ID: No 12), portions thereof, mutants thereof, variants thereof; *Gaussia* Luciferase (the nucleotide sequence is SEQ ID: No 28 and the amino acid sequence is SEQ ID: No 29), portions thereof, mutants thereof, variants thereof; aqeuorin photoproteinm Luciferase (the nucleotide sequence is SEQ ID: No 30, and the amino acid sequence is SEQ ID: No 31), portions thereof, mutants thereof, variants thereof; and bacterial luciferase (the nucleotide sequence is SEQ ID: No 32, and the amino acid sequence is SEQ ID: No 33), portions thereof, mutants thereof, variants thereof; green fluorescent protein (GFP) (SEQ ID No: 19), portions thereof, mutants thereof, variants thereof, and conservatively modified variants; red fluorescent protein (RFP) (SEQ ID No: 20), portions thereof, mutants thereof, variants thereof, and conservatively modified variants; β-galactosidase (SEQ ID No: 21), portions thereof, mutants thereof, variants thereof, and conservatively modified variants; and β-lactamase (SEQ ID No: 22) portions thereof, mutants thereof, variants thereof, and conservatively modified variants; and the like.

The reporter polynucleotide sequence corresponds to the reporter polypeptide. One skilled in the art can determine the reporter polynucleotide sequence based on the reporter polypeptide sequence or vice versa. The reporter polynucleotide sequence can be included in an expression system (e.g., a vector) and expressed in a cell line or in a host.

The term "mutant" is employed broadly to refer to a protein that differs in some way from a reference wild-type protein, where the protein may retain biological properties of the reference wild-type (e.g., naturally occurring) protein, or may have biological properties that differ from the reference wild-type protein. The term "biological property" of the subject proteins includes, but is not limited to, spectral properties, such as emission maximum, quantum yield, and brightness, the ability to catalyze the conversion of a coelenterazine substrate into a luminescent product in the presence of molecular oxygen, and the like; in vivo and/or in vitro stability (e.g., half-life); and the like. Mutants can include single amino acid changes (point mutations), deletions of one or more amino acids (point-deletions), N-terminal truncations, C-terminal truncations, insertions, and the like. Mutants can be generated using standard techniques of molecular biology.

Expression of the Reporter Sequence

As discussed above, the expression of the reporter sequence produces a bioluminescent protein. The bioluminescent protein can interact with a bioluminescence initiating compound to produce (e.g., emission from the bioluminescent protein) a bioluminescent energy.

Bioluminescence Initiating Compound

As mentioned above, the bioluminescent protein is used in conjunction with a bioluminescence initiating compound to produce a radiation emission. The bioluminescence initiating compound can include, but is not limited to, coelenterazine, analogs, and functional derivatives thereof, and D-luciferin analogs, and functional derivatives thereof. Derivatives of coelenterazine include, but are not limited to, coelenterazine 400a, coelenterazine cp, coelenterazine f, coelenterazine fcp, coelenterazine h, coelenterazine hcp; coelenterazine ip, coelenterazine n, coelenterazine O, coelenterazine c, coelenterazine c, coelenterazine i, coelenterazine icp, coelenterazine 2-methyl, and deep blue coelenterazine (DBC) (described in more detail in U.S. Pat. Nos. 6,020,192; 5,968,750 and 5,874,304). In an embodiment, the bioluminescence initiating compound can be D-luciferin when the bioluminescence compound is Firefly Luciferase.

In general, coelenterazines are known to luminesce when acted upon by a wide variety of bioluminescent proteins, specifically luciferases. Useful, but non-limiting, coelenterazines are disclosed in U.S. patent application Ser. No. 10/053,482, filed Nov. 2, 2001, the disclosure which is hereby incorporated by reference in its entirety. Coelenterazines are available from Promega Corporation, Madison, Wis. and from Molecular Probes, Inc., Eugene, Oreg. Coelenterazines may also be synthesized as described for example in Shimomura et al., Biochem. J. 261: 913-20, 1989; Inouye et al., Biochem. Biophys. Res. Comm. 233: 349-53, 1997; and Teranishi et al., Anal. Biochem. 249: 37-43, 1997.

Linkers

It should be noted that peptide linkers could be positioned between one or more of the components of the reporter polynucleotide (e.g., a binding sequence, a promoter sequence, and a reporter sequence) and the activator fusion protein (e.g., a DNA binding domain, an estrogen receptor folding domain, and a transactivation domain). In an embodiment, the GGGGSGGGGS (SEQ. ID No. 34) and/or the GGGGSGGGGSGGGGS peptide linker (SEQ. ID No. 35) can be used between one or more of the components of the reporter polynucleotide and the activator fusion protein.

Additional Methods of Use

In an embodiment, the ligand-regulable transactivation systems and methods described herein can be used to monitor and assess biological interactions by modifying vector constructs (e.g., ER interactions) in a transgenic animal or a transgenic plant.

In another embodiment, a cell line or transgenic animal is marked with vector sets described herein that are developed utilizing coding regions of sequences for the ligand-regulable transactivation system, for example, followed by optical imaging to image and/or quantitate ER related events in the presence and absence of molecules (e.g., pharmaceuticals) designed to modulate the interaction. As will be appreciated by the skilled practitioner, this technique will significantly accelerate drug validation by allowing testing in vivo.

In this regard, the present disclosure also includes transgenic animals comprising exogenous DNA incorporated into the animal's cells to effect a permanent or transient genetic change, preferably a permanent genetic change. Permanent genetic change is generally achieved by introduction of the DNA into the genome of the cell. Vectors for stable integration include plasmids, retroviruses and other animal viruses, YACS, and the like. Generally, transgenic animals are mammals, most typically mice.

The exogenous nucleic acid sequence may be present as an extrachromosomal element or stably integrated in all or a portion of the animal's cells, especially in germ cells.

Unless otherwise indicated, a transgenic animal includes stable changes to the GERMLINE sequence. During the initial construction of the animal, chimeric animals (chimeras) are generated, in which a subset of cells has the altered genome. Chimeras may then be bred to generate offspring heterozygous for the transgene. Male and female heterozygotes may then be bred to generate homozygous transgenic animals.

Typically, transgenic animals are generated using transgenes from a different species or transgenes with an altered nucleic acid sequence. For example, a human gene may be introduced as a transgene into the genome of a mouse or other animal. The introduced gene may be a wild-type gene, naturally occurring polymorphism, or a genetically manipulated sequence, for example having deletions, substitutions or insertions in the coding or non-coding regions.

For example, an introduced transgene may include genes corresponding to the ER folding system, which may become functional via complementation or reconstitution when exposed to appropriate test proteins or, alternatively, which may become non-functional when exposed to a particular test protein that blocks phosphorylation. Such a transgene, when introduced into a transgenic animal or cells in culture, is useful for testing potential therapeutic agents known or believed to interact with a particular target protein implicated in a disease or disorder. Where the introduced gene is a coding sequence, it is usually operably linked to a promoter, which may be constitutive or inducible, and other regulatory sequences required for expression in the host animal.

Transgenic animals can be produced by any suitable method known in the art, such as manipulation of embryos, embryonic stem cells, etc. Transgenic animals may be made through homologous recombination, where the endogenous locus is altered. Alternatively, a nucleic acid construct is randomly integrated into the genome. Vectors for stable integration include plasmids, retroviruses and other animal viruses, YACS, and the like.

Numerous methods for preparing transgenic animals are now known and others will likely be developed. See, e.g., U.S. Pats. Nos. 6,252,131, 6,455,757, 6,028,245, and 5,766,879, all incorporated herein by reference. Any method that produces a transgenic animal expressing a reporter gene following complementation or reconstitution is suitable for use in the practice of the present invention. The microinjection technique is particularly useful for incorporating transgenes into the genome without the accompanying removal of other genes.

Kits

This disclosure encompasses kits that include, but are not limited to, a ligand-regulable transactivation system or vectors thereof; a bioluminescence initiating compound; and directions (written instructions for their use). The components listed above can be tailored to the particular biological event (e.g., ER related events) to be monitored as described herein. The kit can further include appropriate buffers and reagents known in the art for administering various combinations of the components listed above to the host cell or host organism. The components of the present disclosure and carrier may be provided in solution or in lyophilized form. When the components of the kit are in lyophilized form, the kit may optionally contain a sterile and physiologically acceptable reconstitution medium such as water, saline, buffered saline, and the like.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

Example

Now having described the embodiments of the disclosure, in general, the example describes some additional embodiments. While embodiments of present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Introduction

Figure 1:
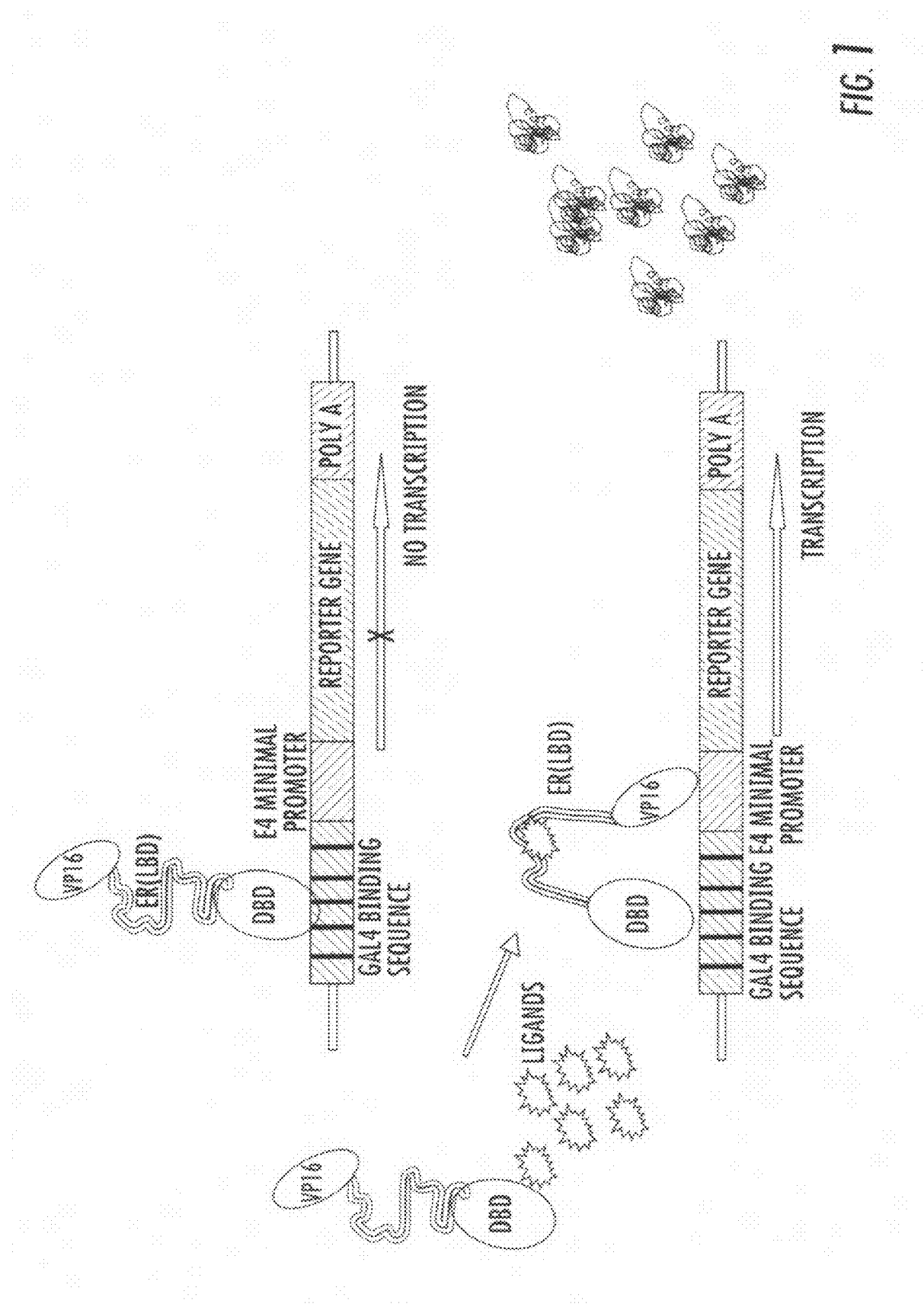
FIG. 1 is a schematic of the ligand induced transactivation system developed. In this system ER ligand binding domain is expressed in between the GAL4 DNA binding domain and the VP16 transactivation domain as a fusion protein. The GAL4 DNA binding domain from the expressed fusion protein binds to its specific binding DNA sequence present in the co-delivered reporter vector. The ER (LBD) in the fusion protein is in a different conformation when it is in a ligand free form and it keeps the VP16 transactivation domain away from the minimal promoter. When the ligand is available the ER (LBD) binds with the ligand and leads to a conformational change that brings VP16 portion of the fusion protein near the promoter minimal E4 and leads to the activation of gene transcription.

In this Example the property of estrogen receptor that usually changes its conformation in response to its ligand bindings, that specifically brings the N- and C-termini of the protein near by each other, is used in combination with the HSV1-VP16 transactivator and the Yeast DNA binding domain, to develop the current ligand-regulable transactivation system. This Example illustrates the use of the ligand binding domain of estrogen receptor as used in a fusion protein with the GAL4 binding domain and VP16 transactivation domain on either side (FIG. 1). The system was studied in cells and cell implants in living animals by non-invasive imaging. It was also shown that this system can be activated by different ER-ligands and the mutant form developed is independent of binding with the endogenous ligand. In addition, by controlling the length of ER-ligand binding domain, a system that can differentiate ER-ligands as agonist and antagonist was developed. Further, a mutant form of ER was used form a system that specifically showed low affinity for endogenous ER-ligand 17β-estradiol for the extension of this system in living animals.

Results

Development of ER-ligand induced transactivation system. To develop an ER-ligand induced transactivation system, a series of vectors were constructed that constitutively express fusion proteins containing a Yeast GAL4-DNA binding domain and a transactivator peptide of human herpes simplex virus type 1 (HSV1-VP16) with ER-ligand binding domains of different lengths. These vectors were used in combination with the reporter vector flanking five times repeats of a Yeast GAL4-DNA binding sequence, an E4 minimal promoter and the reporter gene of choice, for different co-transfection experiments. As a positive control, a vector constitutively expressing fusion protein containing a Yeast DNA binding domain directly fused to a HSV1-VP16-transactivator peptide (hereinafter, this will be stated as constitutive transactivation system) was used. Both of these systems were studied in different cell lines and cell implants in living animals (FIG. 1).

Figure 2:
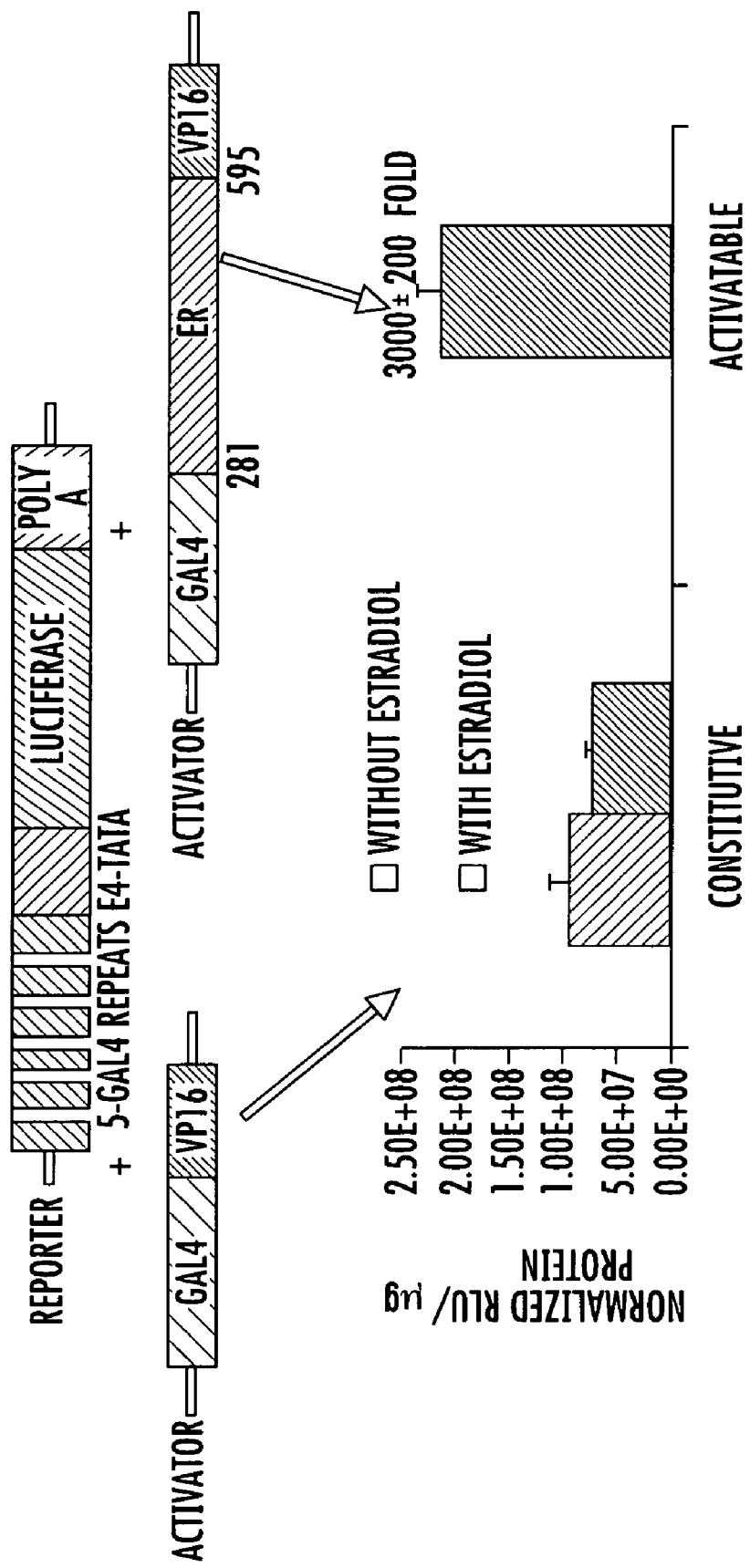
FIG. 2 is a graph of a comparison of ligand induced transactivation system with the constitutive transactivation system. To compare the ER-ligand induced transactivation system with the constitutive transactivation system, 293T cells co-transfected with the reporter plasmid with either activator expressing fusion protein containing GAL4, ER and VP16 or expressing GAL4 and VP16 alone were assayed for luciferase activity before and after exposure to 1 µM concentration ligand 17-β estradiol. The ligand induced transactivation system showed significant level of activity only when receiving the ligands ($p<0.001$).

Comparison of ER-ligand induced transactivation system with the constitutive transactivation system in transiently transfected 293T cells. To study the efficiency of ER-ligand induced transactivation system, the system was compared with the constitutive transactivation system in transiently transfected 293T cells before and after exposed to 1 µM concentration of ER-ligand 17β-estradiol. The result shows significant level of luciferase signal from the cells transfected with the constitutively active system both before and after exposed to ligand 17β-estradiol ($p<0.001$). At the same time the cells transfected with the activatable system shows luciferase signal only from the cells exposed to 17β-estradiol ($p<0.001$). The cells transfected with the activatable system exposed to carrier control (DMSO) shows signal that is slightly above the mock-transfected cells (FIG. 2).

Figure 3:
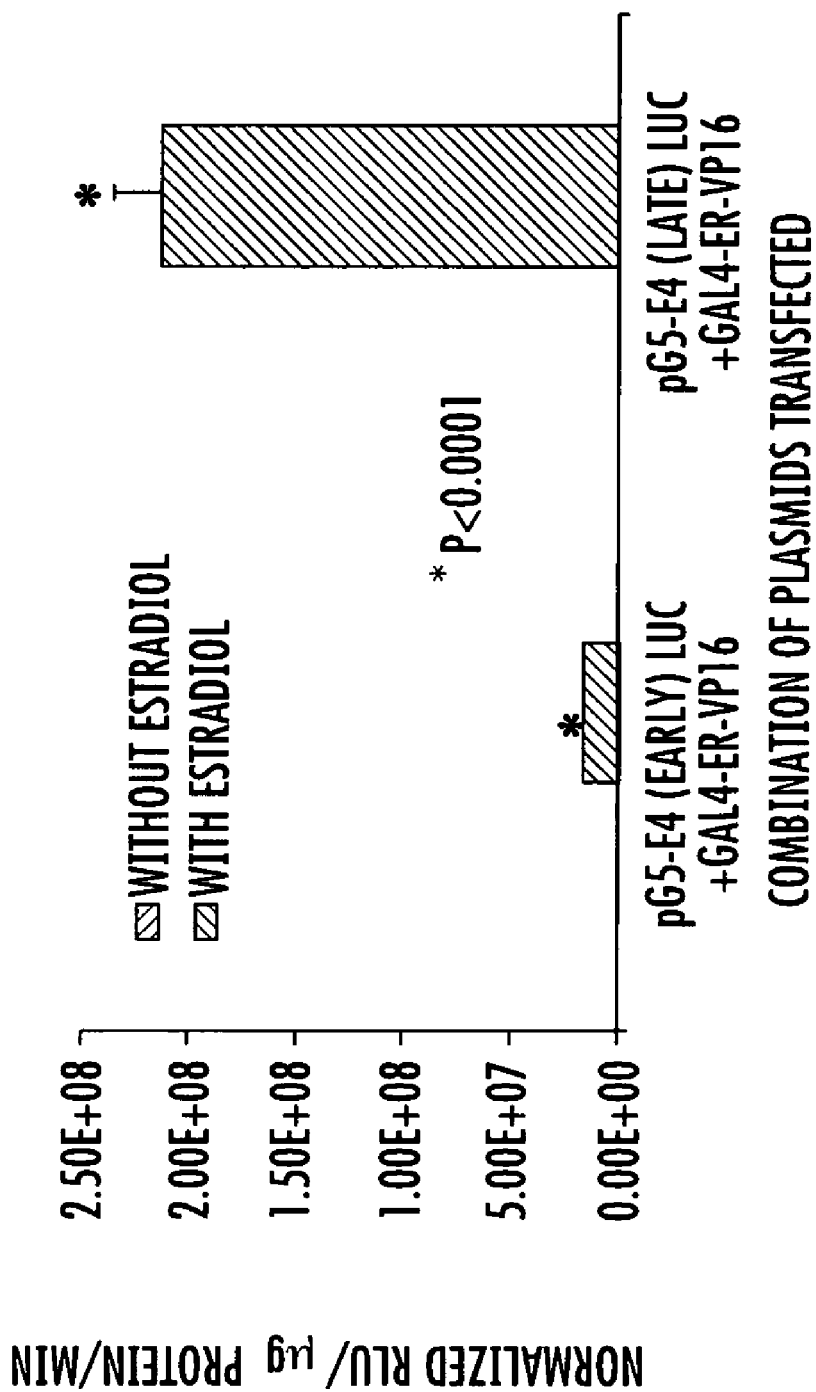
FIG. 3 is a graph of a comparison ligand induced transactivation system with adenoviral early and late minimal promoters. The 293T cells transiently co-transfected with reporter plasmid contain GAL4 DNA binding sequence followed by adenoviral early and late minimal promoters driving firefly luciferase and plasmid expressing GAL4-ER-VP16 under CMV promoter. The cells were assayed for luciferase activity with and without exposure to ligand 17-β estradiol.

Comparison of estrogen receptor ligand induced transactivation system with adenoviral early and late minimal promoters. To compare the efficiency of adenoviral early and late minimal promoters in ligand induced transactivation system, the 293T cells co-transfected with the system containing these promoters were analyzed for luciferase activity before and after exposed to 1 µM concentration of ligand 17β-estradiol. The result shows significant level of activity from both the systems only after exposed to ligand 17β-estradiol ($p<0.0001$). The system containing the adenoviral late promoter shows luciferase activity that is significantly greater than with the system containing the early promoter ($p<0.01$: 10±3 fold). When the cells are exposed to ligand 17β-estradiol, the signal increased 3,000±200 fold more than the cells not exposed to 17β-estradiol ($1.8\pm0.4\times10^8$ RLU/µg Protein Vs $6.0\pm1.8\times10^4$) (FIG. 3).

Ligand concentration dependent activation of reporter gene expression in transiently transfected 293T and CHO cells. To check the system dose dependent response to different concentrations of ligand, 293T and CHO cells transiently co-transfected with the activator and the reporter plasmids were activated with several concentrations of 17β-estradiol ranged from 0 to 1 µM. The result shows concentration dependent increase in the level of reporter gene expression in both the cell lines used for the study. It shows significant correlation between the concentration of ligand used and the luciferase signal produced (CHO: $R^2=0.9063$; 293T: $R^2=0.9581$) (FIG. 4).

Transactivation of reporter gene expression by different ER-ligands. In addition to the ligand concentration dependent activation of reporter gene expression by 17β-estradiol, this system has advantage in the availability of several ligands. Hence, to study the utility of other ligands in activating the system, 293T cells transiently co-transfected with the activator and the reporter plasmids were exposed to 1 µM concentration of 7 different ER-ligands including a non-ligand anti-cancer drug. The system shows significant levels of transactivation by all of the different ER-ligands used for the study ($p<0.001$). At the same time the non-ligand anticancer drug shows signal that is not significantly different from the cells exposed to carrier control. Even though all the ER-ligands showed significant levels of activation upon the system, the level of induction was different for each ligand. The fold luciferase signal produced by different ER-ligands in comparison to carrier control are; Raloxifene: 2800±400, Tamoxifen: 2000±300, 4-hydroxy tamoxifen: 3000±500, Genistein: 600±100, Diethylstilbestrol: 2200±300, 17β-estradiol: 2400±100 and ICI: 300±80 (FIG. 5a). To confirm the ligand induced increase in the level of reporter protein is due to the ER-folding mediated transactivation, 293T cells co-transfected with the reporter and activator plasmids were Western blot analyzed after inducing with various ligands for 18 h for both the reporter protein and the activator fusion chimera. The result shows the increase in the level of reporter protein expression is not due to the increase in the activator protein level. It is due to the change in the ligand induced folding in ER and the following activation in response to ligands (FIG. 5b).

Efficiency of ligand induced transactivation system in activating the reporter gene expression in a bi-directional vector. To check the utility of ligand induced transactivation system in regulating two reporter genes expressing in two different directions, the plasmid vector expressing the activator fusion protein chimera containing ER was used along with the bi-directional vector developed and evaluated previously (Ray, S. et al. A Novel Bi-Directional Vector Strategy for Amplification of Therapeutic and Reporter Gene Expression. *Human Gene Therapy* (2004), which is incorporated herein by reference). Co-transfection of these two vectors in 293T cells were assayed for both firefly and *renilla* luciferases after exposed to different concentrations of ligand 17β-estradiol for 18 h. The result shows ligand concentration dependent increase by both the reporters. The analysis of the expression levels of two reporters in response to different concentrations of ligand shows highly significant correlation ($R^2=0.9936$) (FIGS. 6A and 6B).

Ligand induced transactivation system to differentiate ER-ligands. As the estrogen receptor was used to develop the current ligand induced transactivation system for the controlled expression of transgenes, this study was extended for adopting the systems utility in screening new ER-ligands and also modified the system to differentiate ER-ligands as agonists and antagonists. From our previous study it was learned that by adjusting the length of ER-ligand binding domain; it will be possible to change the folding pattern of ER in response to different ligands and its associated reporter fragment complementation (under communication). The same strategy was used in this study and achieved similar result. An activator plasmid expressing the fusion protein chimera was constructed and contained the ER of amino acids from 281 to 549. The system was studied in transiently co-transfected 293T cells by exposing to different ER-ligands (agonist, antagonist, partial agonists and partial antagonists) (FIG. 7).

Ligand induced transactivation system with mutant form of ER-ligand binding domains. To extend this system utilization in living animals, the problem of endogenous estrogen that usually interferes was considered. A mutant form of estrogen receptor $hER_{G521T}$ was identified with specifically low affinity to 17β-estradiol. The system with the mutant form of ER showed significant level of activity without loosing any activity for other ligands (FIG. 8).

Imaging ligand induced transactivation system in living animals. To image ligand induced transactivation system in living animals, the 293T cells transiently co-transfected with the reporter and the activator plasmids expressing fusion chimera containing the mutant form of ER (G521T/amino acids 281-599) were implanted subcutaneously in living mice (site B). The 293T cells co-transfected with the reporter and the constitutive active activator were used as control (site A). The animals (n=3 each for control and experiment group) were imaged in 24 h intervals by alternate injection of ligand Raloxifene for the experiment group. The results show no luciferase signal immediately after implanting the cells. After 24 h the animal received drug Raloxifene and produced signal that is significantly greater than the control group (p<0.001). The cells implanted with the constitutive active system showed signal that is significant both before and after injecting ligand Raloxifene in experimental group and also in control group. The system showed efficient ligand regulable gene expression in mice implanted with 293T cells transiently transfected with the reporter and the activator plasmids. The level of signal achieved before induced with the ligand was not significantly above the background. When induced with 0.5 mg of Raloxifene the reporter luciferase gene expression reached 15±5 fold more. The system showed efficient on/off mechanism in response to ligand Raloxifene (FIG. 9).

Materials and Methods

Chemicals, Enzymes and Reagents. Restriction and modification enzymes and ligase were from New England Biolabs (Beverly, Mass.). TripleMaster Taq DNA polymerase from Brinkmann Eppendorf (Hamburg, Germany) was used for the PCR amplification of different fragments used for constructing different vectors used in this study. PCR was used for the amplification of genes of different reporters and the estrogen receptor alpha of human (hERα/HE0). Different estrogen receptor antagonists and agonists include Tamoxifen, 4-hydroxytamoxifen, Raloxifene, Diethylstilbestrol, 17β-estradiol, Genistein, anticancer drugs cisplatinum and Green Tea, and antibiotics for bacterial cultures were from Sigma (St. Louis, Mo.). Lipofectamine transfection reagent was from Invitrogen (Carlsbad, Calif.). The plasmid extraction kit and DNA gel extraction kit were purchased from Qiagen (Valencia, Calif.). Coelenterazine was from Nanolight (Pinetop, Ariz.). Bacterial culture media were from BD Diagnostic Systems (Sparks, Md.). All cell culture media, fetal bovine serum, the antibiotics streptomycin, and penicillin, were from Invitrogen (Carlsbad, Calif.). The plasmids for Tet-on system were from Clontech (Valencia, Calif.). The custom oligonucleotides synthesized from Stanford Protein and Nucleic acid (PAN) facility were used as primers for the amplification different fragments of genes, reporters and for making different amino acid linkers. The Stratagene (La Jolla, Calif.) site directed mutagenesis kit was used for constructing the mutant ligand-binding domain of estrogen receptor. DAN sequencing were from PAN facility, Stanford and Sequetech (Mountain view, Calif.).

Construction of Plasmids. The unidirectional and bi-directional reporter vector containing five GAL4 DNA binding sites and the adenovirus early minimal promoter E4 were from our previous studies (Ray, S. et al. Novel bidirectional vector strategy for amplification of therapeutic and reporter gene expression. *Hum Gene Ther* 15, 681-690 (2004); Iyer, M. et al. Two-step transcriptional amplification as a method for imaging reporter gene expression using weak promoters. *Proc Natl Acad Sci USA* 98, 14595-14600 (2001), both of which are incorporated herein by reference). The reporter plasmid containing five GAL4 DNA binding site and the major late promoter of adenovirus from Promega (Madison, Wis.) was used for the comparison. The vector construct expressing the fusion protein contain GAL4 DNA binding domain, ER of different lengths and the transactivator VP16 was constructed by inserting PCR amplified fragments of ER to the Eco RI and Bam HI digested activator plasmid from the previous study. The mutant forms of ER were constructed by using the site directed mutagenesis kit of Stratagene (FIG. 1).

Cell Culture. Human 293T embryonic kidney cancer cells (ATCC, Manassas, Va.) were grown in MEM supplemented with 10% FBS and 1% penicillin/streptomycin solution. The estrogen receptor positive human breast cancer cells MCF7 and the estrogen receptor negative cells MDA-MB231 were grown in RPMI 1640 and DMEM high glucose respectively supplemented with 10% FBS and 1% penicillin/streptomycin. CHO cells were grown in Ham F12K medium supplemented with 10% FBS and 1% penicillin/streptomycin. The cells used for transactivation using ER ligands were grown in activated charcoal treated serum from HyClone (Logan, Utah).

Cell Transfection and Luciferase Assay. Transfections were performed in 80% confluent 24 h old cultures of 293T and CHO cells. For transfections, unless specified, 200 ng/well DNA were used in 12 well culture plates. Volumes of Lipofectamine were as recommended by the manufacturer. For induction, different ER ligands dissolved in DMSO or doxycycline dissolved in water to concentrations of 1 µM and 1 µg/ml respectively were used. Drugs were added immediately after transfection. The cells were assayed after 24 h incubation at 37° C. and in 5% $CO_2$. The luminometry assay for $Renilla$ luciferase activity was performed as per protocol published previously (Bhaumik, S. & Gambhir, S. S. Optical imaging of $Renilla$ luciferase reporter gene expression in living mice. $Proc\ Natl\ Acad\ Sci\ USA$ 99, 377-382 (2002), which is incorporated herein by reference). For firefly luciferase assay 20 µl of samples lysed in passive lysis buffer were mixed with 100 µl luciferase assay reagent II (LAR II) from Promega and counted for 10 sec in the luminometer (Turner 20/20, Sunnyvale, Calif.). Measuring the protein concentration in the cell lysates normalized the readings. Activities of FLUC and RLUC were represented as relative light units (RLU) per microgram of protein.

Studying the ER ligand induced transactivation in transiently transfected 293T cells. To study the ER ligand induced transactivation of reporter gene expression, the 293T cells co-transfected with 200 ng/well each of the reporter plasmid (pGL-G5-E4-Fluc) and the activator plasmid expressing GAL4-ER-VP16 were used. The cells were assayed for luciferase activity 24 h after exposure to 1 µM concentration of ligand 17β-estradiol (E2). The transfection efficiency was normalized by co-transfecting with 10 ng of $Renilla$ luciferase expressing under CMV promoter in all the required experiments.

Studying the ligand concentration dependent transactivation of reporter gene expression in transiently transfected 293T and CHO cells. To study the ligand induced transactivation in a concentration dependent manner, the 293T cells were co-transfected with different reporter and activator ratio (1:1 to 1:0.1) and assayed for luciferase activity after exposure to different concentrations of 17β-estradiol (0 to 1.5 µM).

Studying different ER agonists and antagonists induced transactivation of reporter gene expression in transiently transfected 293T human embryonic kidney cancer cells and ER negative MDA-MB231 breast cancer cells. To study the impact of different ER ligands in the transactivation of reporter gene expression, the 293T and MDA-MB231 cells transiently co-transfected with the reporter (200 ng/well in 12 well culture plate) and activator (20 ng/well in 12 well culture plate) plasmids were assayed for luciferase activity 24 hours after exposure to 1 µM each separately by 17β-estradiol, 4-hydroxytamoxifen, Tamoxifen, Raloxifene, Genistein, Diethylstilbestrol, and solvent DMSO and anticancer drug Cisplatinum controls.

Comparing the efficiency of ER-ligand induced transactivation system with the constitutive active GAL4-VP16 system in transiently transfected 293T cells. To compare the efficiency of the ER ligand induced transactivation system with the previously used constitutive GAL4-VP16 system, the 293T cells co-transfected with reporter-pGL-G5-E4-Fluc and activator-pGAL4-VP16, or co-transfected with the reporter-pGL-G5-E4-Fluc and activator-pGAL4-ER-VP16 after inducing with ligand 17β-estradiol were assayed 24 hours after incubation for luciferase activity.

Ligand regulated transactivation system in the expression of reporter gene in a bi-directional vector in two different orientations. To study the efficiency of controlling the two reporter genes expressed in two different orientations in a single plasmid, the 293T cells transiently co-transfected with the reporter plasmid (pGL-G5-E4-Fluc-Rluc) and activator plasmid (pGL-GAL4-ER-VP16) in 1:0.1 ratio were exposed to different concentrations of 17β-estradiol (0, 0.006, 0.012, 0.0235, 0.047, 0.094, 0.1875, 0.375, 0.75 and 1.5 µM) and assayed for Fluc and Rluc activities. Estimating the $R^2$ value assessed the correlation between the two enzymes level.

Ligand induced transactivation system to differentiate ER-ligands. To make the ligand induced transactivation system that can differentiate ER-ligands, the ER-LBD of different length (281-549) identified from our previous study (under communication) was used to replace the ER of 281-595. The system was studied in transiently co-transfected 293T cells by exposing to 1 µM concentrations of different ligands. The cells were lysed and assayed for luciferase activity after 24 h.

Imaging ligand induced transactivation system in living animals. All animals handling was performed in accordance with Stanford University Animal Research Committee guidelines. For imaging in living nude mice (nu/nu), 293T cells transiently co-transfected with reporter plasmid and the activator plasmid expressing GAL4-VP16 fusion protein for constitutive active system, and reporter plasmid with the activator plasmid expressing fusion protein GAL4-ER-VP16 for activatable system were used. Animals implanted with 10 million cells of each system on the back of living mice were imaged by injecting 3 mg of substrate D-luciferin. For activatable system animals were imaged periodically before and after injecting ligand Raloxifene.

Discussion

This Example provides an efficient ligand regulable transcriptional amplification system that has multiple applications. This system showed greater efficiency in controlling the expression level of transgenes both in cells and xenografts in living animals. This system can also be used to screen new ER-ligands with therapeutic potential from both natural and synthetic sources. The system can be used to distinguish and differentiate ER-ligands as agonist, antagonist, partial antagonist, and partial agonist.

From our previous study it was learned that ER can lead to intramolecular folding and following split luciferase complementations when it binds with its ligands (communicated). This was extended to develop the current ligand mediated transactivation system. In addition we also learned from our earlier study that the orientation and the distance between the N- and C-terminus of ER is differentially positioned when it binds with its ligands. Extending the length of C-terminus of the protein by adding more amino acids either from the remaining portion of the protein or by choice can also change this. So this property of the receptor in modifying the system for differentiating ER-ligands was studied.

There are several systems available for regulating transgene expression in cells and also in living animals. In contrast to the present system, most of the strategy suffers due to greater level of background or due to the toxic nature of the chemicals used for inducing the system.

There are several drugs in the market that can work as agonists or antagonists in the modulation of the estrogen receptor and other steroid receptors super family. In particular, the agonist and antagonist of estrogen receptors bind in the same ligand-binding domain with a different binding mode. But each of these ligands induces a specific conformation in the transactivation domain and leads to different downstream gene activation. As discussed in the previous section, the helix H12 is an important portion of the estrogen receptor that has different conformational changes in response to different ligands. The controls of gene transcription of many cellular genes are the indications of cell growth and development and malignant transformations. The effects of these steroid hormones including estrogens, testosterones, thyroid hormones, retinoids, ecdysone, prostaglandins and oxygenated cholesterols are mediated through specific receptors proteins termed as steroid/nuclear receptor, which are still not completely studied. The uniqueness of ER among these different steroid receptor super family receptors is in sensing many of the structurally non-steroidal compounds. There is currently no system available that can easily distinguish between agonists and antagonists based on its ligand bindings and associated conformational changes. It is also important to screen more number of Selective Estrogen Receptor Modulators (SERM) as anticancer drugs.

The extreme abundance of localized temporary, or more stable protein homodimers attests to their many functions in the cell and the important role they play in many biological processes. The ability to detect, locate, and quantify protein homodimerization in the setting of a whole living animal model has important implications for a wide variety of biological research endeavors, drug discovery, and molecular medicine. In particular, the visual representation, characterization, and quantification of these biological processes in living subjects now creates unprecedented opportunities to complement available in vitro or cell culture methodologies, in order: (i) to characterize more fully known homodimeric protein-protein interactions in the context of whole-body physiologically-authentic environments, and (ii) to accelerate the evaluation in living animal models of novel drugs that promote or inhibit active homodimeric protein assembly.

The ligand-induced conformation of a nuclear receptor ligand-binding domain is a principal factor leading to transcriptional activity and determining the pharmacological response. Even though many studies have dealt with the transcriptional activation of target genes in response to ligands, only a few have attempted in distinguishing the conformational difference in response to agonists and antagonists. The study using fluorescent labeling of specific amino acids (417 and 435) in the ligand-binding domain has been studied. The system developed from this study is not only useful for regulating transgenes expression it will also be useful in studying more about the mystery behind the biology of ER.

We claim the following:

1. A method of detecting a ligand in vitro, comprising:
   providing a ligand-regulable transactivation system comprising:
   a reporter polynucleotide that comprises a binding sequence, a promoter sequence, and a reporter sequence encoding a detectable bioluminescent protein, wherein the binding sequence is connected with the promoter sequence and the promoter sequence is connected with the reporter sequence; and
   an activator fusion protein that comprises:
   a DNA binding domain capable of interacting with the binding sequence of the reporter polynucleotide, an estrogen receptor folding domain (ER folding domain) capable of binding a ligand, wherein the ER folding domain is selected from: a sequence consisting of SEQ ID NO:1 (human estrogen receptor, alpha, amino acids 281-549), a sequence consisting of SEQ ID NO:2 (human estrogen receptor, alpha, amino acids 281-595), a sequence consisting of SEQ ID NO:4 (mouse estrogen receptor, alpha, amino acids 281-549), a sequence consisting of SEQ ID NO:5 (mouse estrogen receptor, alpha, amino acids 281-599), SEQ ID NO:23 and SEQ ID NO:24, and
   a transactivation domain capable of interacting with the promoter sequence of the reporter polynucleotide,
   wherein the DNA binding domain is connected to the estrogen receptor folding domain, and the estrogen receptor folding domain is connected with the transactivation domain, and wherein interaction of the DNA binding domain and the transactivation domain of the activator fusion protein with the binding sequence and promoter sequence of the reporter polynucleotide regulates expression of the detectable bioluminescent protein;
   introducing a ligand to the system; and
   detecting a bioluminescent signal in the presence of a bioluminescence initiating compound if the ligand causes the ER folding domain to change from a non-interacting conformational position to an interacting conformational position, wherein the interacting conformational position positions the DNA binding domain and the transactivation domain of the activator fusion protein so that both interact with the binding sequence and the promoter sequence of the reporter polynucleotide, which causes expression of the detectable bioluminescent protein encoded by the reporter sequence.

2. The method of claim 1, wherein the ligand is selected from: ER ligands, ER agonists, partial ER agonists, ER antagonists, partial ER antagonists, and selective estrogen receptor modulators.

3. The method of claim 1, wherein the interacting conformation position corresponds to one of two states including substantially interacting and partially interacting, wherein substantially interacting means that the DNA binding domain and the transactivation domain interact with the binding sequence and the promoter sequence of the reporter polynucleotide to generate a first amount of bioluminescent protein, and wherein partially interacting means that the DNA binding domain and the transactivation domain interact with the binding sequence and the promoter sequence of the reporter polynucleotide to generate a second amount of bioluminescent protein, wherein the first amount of bioluminescent protein is greater than the second amount of bioluminescent protein.

4. The method of claim 1, wherein the reporter sequence is selected from polynucleotide sequences encoding one of the following: a luciferase and a photoprotein.

5. The method of claim 1, wherein the reporter sequence is selected from polynucleotide sequences encoding one of the following: a *Renilla* Luciferase; a Coleoptera Luciferase; a Firefly Luciferase; a *Gaussia* Luciferase; and an aequorin photoprotein Luciferase.

6. The method of claim 1, wherein the promoter sequence is selected from: an E4 promoter (SEQ ID NO:36), an E4 minimal promoter (SEQ ID NO:18), minimal promoter thymidine kinase (tk-promoter) (SEQ ID NO:18), and an adenoviral late promoter (SEQ ID NO:38).

7. The method of claim 1, wherein the binding sequence is a GAL4 binding sequence (SEQ ID NO:17).

8. The method of claim 1, wherein the DNA binding domain is GAL4 DNA binding domain (SEQ ID NO:14).

9. The method of claim 1, wherein the transactivation domain is VP16 transactivation domain (SEQ ID No: 16).

10. The method of claim 1, wherein the ligand-regulable transactivation system is expressed in an isolated living cell or culture of cells.

11. A method of detecting a ligand in vivo, comprising:
implanting cells into a nude mouse, wherein the cells comprise exogenous polynucleotides expressing a ligand-regulable transactivation system comprising:
a reporter polynucleotide that comprises a GAL 4 binding sequence, a promoter sequence, and a reporter sequence encoding a detectable bioluminescent protein, wherein the binding sequence is connected with the promoter sequence and the promoter sequence is connected with the reporter sequence; and
an activator fusion protein that comprises:
a DNA binding domain capable of interacting with the binding sequence of the reporter polynucleotide,
an estrogen receptor folding domain (ER folding domain) capable of binding a ligand, wherein the ER folding domain is selected from: SEQ ID NO:23 and SEQ ID NO:24, and
a VP16 transactivation domain capable of interacting with the promoter sequence of the reporter polynucleotide,
wherein the DNA binding domain is connected to the estrogen receptor folding domain, and the estrogen receptor folding domain is connected with the transactivation domain, and wherein interaction of the DNA binding domain and the transactivation domain of the activator fusion protein with the binding sequence and promoter sequence of the reporter polynucleotide regulates expression of the detectable bioluminescent protein;
introducing a ligand to the animal, wherein the ligand is not an endogenous ligand in the mouse; and
detecting a bioluminescent signal in the presence of a bioluminescence initiating compound if the ligand causes the ER folding domain to change from a non-interacting conformational position to an interacting conformational position, wherein the interacting conformational position positions the DNA binding domain and the transactivation domain of the activator fusion protein so that both interact with the binding sequence and the promoter sequence of the reporter polynucleotide, which causes expression of the detectable bioluminescent protein encoded by the reporter sequence.

12. The method of claim 11, wherein the ligand is selected from: ER ligands, ER agonists, partial ER agonists, ER antagonists, partial ER antagonists, and selective estrogen receptor modulators.

13. The method of claim 11, wherein the interacting conformation position corresponds to one of two states including substantially interacting and partially interacting, wherein substantially interacting means that the DNA binding domain and the transactivation domain interact with the binding sequence and the promoter sequence of the reporter polynucleotide to generate a first amount of bioluminescent protein, and wherein partially interacting means that the DNA binding domain and the transactivation domain interact with the binding sequence and the promoter sequence of the reporter polynucleotide to generate a second amount of bioluminescent protein, wherein the first amount of bioluminescent protein is greater than the second amount of bioluminescent protein.

14. The method of claim 11, wherein the reporter sequence is selected from polynucleotide sequences encoding one of the following: a luciferase and a photoprotein.

15. The method of claim 11, wherein the reporter sequence is selected from polynucleotide sequences encoding one of the following: a *Renilla* Luciferase; a Coleoptera Luciferase; a Firefly Luciferase; a *Gaussia* Luciferase; and an aequorin photoprotein Luciferase.

16. The method of claim 11, wherein the promoter sequence is selected from: an E4 promoter (SEQ ID NO:36), an E4 minimal promoter (SEQ ID NO:18), minimal promoter thymidine kinase (tk-promoter) (SEQ ID NO:18), and an adenoviral late promoter (SEQ ID NO:38).

17. The method of claim 11, wherein the VP16 transactivation domain has the sequence of SEQ ID NO:16.

18. A method of detecting a ligand in vitro, comprising:
providing a ligand-regulable transactivation system comprising:
a reporter polynucleotide that comprises a GAL4 binding sequence of SEQ ID NO:17, a promoter sequence, and a reporter sequence encoding a detectable bioluminescent protein, wherein the binding sequence is connected with the promoter sequence and the promoter sequence is connected with the reporter sequence; and
an activator fusion protein that comprises:
a DNA binding domain capable of interacting with the GAL4 binding sequence of the reporter polynucleotide,
an estrogen receptor folding domain (ER folding domain) capable of binding a ligand, and
a transactivation domain capable of interacting with the promoter sequence of the reporter polynucleotide,
wherein the DNA binding domain is connected to the estrogen receptor folding domain, and the estrogen receptor folding domain is connected with the transactivation domain, and wherein interaction of the DNA binding domain and the transactivation domain of the activator fusion protein with the binding sequence and promoter sequence of the reporter polynucleotide regulates expression of the detectable bioluminescent protein;
introducing a ligand to the system; and
detecting a bioluminescent signal in the presence of a bioluminescence initiating compound if the ligand causes the ER folding domain to change from a non-interacting conformational position to an interacting conformational position, wherein the interacting conformational position positions the DNA binding domain and the transactivation domain of the activator fusion protein so that both interact with the binding sequence and the promoter sequence of the reporter polynucleotide, which causes expression of the detectable bioluminescent protein encoded by the reporter sequence.

19. The method of claim 18, wherein the estrogen receptor folding domain is selected from: SEQ ID NO:1 (human estrogen receptor, alpha, amino acids 281-549), SEQ ID NO:2 (human estrogen receptor, alpha, amino acids 281-595), SEQ ID NO:3 (human estrogen receptor, alpha, amino acids 1-595), SEQ ID NO:4 (mouse estrogen receptor, alpha, amino acids 281-549), SEQ ID NO:5 (mouse estrogen receptor, alpha, amino acids 281-599), SEQ ID NO:6 (mouse estrogen receptor amino acids 1-599), SEQ ID NO:23 and SEQ ID NO:24.

* * * * *